United States Patent [19]
Brooks et al.

[11] Patent Number: 5,795,900
[45] Date of Patent: Aug. 18, 1998

[54] SYMMETRICAL BIS-HETEROARYL-METHOXY-PHENYLALKYL CARBOXYLATES AS INHIBITORS OF LEUKOTRIENE BIOSYNTHESIS

[75] Inventors: Clint D. Brooks; Pramila Bhatia, both of Libertyville; Teodozyj Kolasa, Lake Villa; Andrew O. Stewart, Libertyville, all of Ill.; David E. Gunn, Hamden, Conn.; Richard A. Craig, Racine, Wis.

[73] Assignee: Abbott Laboratories, Abbott Park, Ill.

[21] Appl. No.: 703,441

[22] Filed: Sep. 17, 1996

Related U.S. Application Data

[60] Provisional application No. 60/004,706, Oct. 3, 1995.
[51] Int. Cl.$^6$ .............. C07D 213/30; C07D 215/14; C07D 401/10; A61K 31/47
[52] U.S. Cl. .............. 514/314; 546/153; 546/174; 546/175; 546/176; 546/180
[58] Field of Search .............. 514/314; 546/174, 546/175, 176, 180, 153

[56] References Cited

U.S. PATENT DOCUMENTS

| | | | |
|---|---|---|---|
| 4,970,215 | 11/1990 | Mohrs et al. | 514/311 |
| 5,326,883 | 7/1994 | Brooks | 549/65 |
| 5,358,955 | 10/1994 | Brooks et al. | 514/311 |
| 5,512,581 | 4/1996 | Brooks et al. | 514/311 |

FOREIGN PATENT DOCUMENTS

| | | |
|---|---|---|
| 0349062 | 6/1989 | European Pat. Off. |
| 9427968 | 8/1994 | WIPO |

OTHER PUBLICATIONS

P. Prasit; A New Class of Leukotriene Biosynthesis Inhibitors: The Development of ((4O(4–Chlorophenyl)-1(4–(–Quinolinylmethoxy)Phenyl)Butyl)Thio)Acetic Acid, L–674,636 Biorganic & Medicinal Chemistry Letters, vol. 1, No. 11, pp. 645–648, 1991.

Musser et al; 5–Lipoxygenase: Properties, Pharmacolgy, and The Quinolinyl (Bridged) Aryl Class of Inhibitors; Journ of Med Chem 1992, vol. 35, No. 14 pp. 2501–2524.

A.J. Mancuso,et al. Oxidation of Long–Chain and Related Alcohols to Carbonyls by Dimethyl Sulfoxide "Activated" by Oxalyl Chloride J. Org. Chem., vol. 43,No. 12, 1978, pp. 2480–2482.

O. Mitsunobu, Sunthesis International Journal of Methods in Synthetic Organic Chemistry 1981 No. 1: Jan., pp. 1–28.

S. Berge, et al. Pharmaceutical Salts, Journal of Pharm Sciences Jan 1977 vol 66 No. 1, pp. 1–19.

T. Rao et al. Evaluation of 5–Liboxygenase Inhibitors, Zileuton, A–78773 and ICI–D–2138 in an Ionophore (A–23187) Induced Pleural Inflamation Model in the Rat, Life Sciences, vol. 53, pp. PL 147–152, 1993.

*Primary Examiner*—C. Warren Ivy
*Assistant Examiner*—D. Margaret M. Mach
*Attorney, Agent, or Firm*—Frank Z. Yang

[57] ABSTRACT

Compounds having the formula:

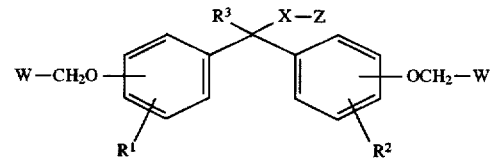

wherein W is the same at each occurrence and is selected from optionally substituted quinolyl, optionally substituted benzothiazolyl, optionally substituted benzoxazolyl, optionally substituted benzimidazolyl, optionally substituted quinoxalyl, optionally substituted pyridyl, optionally substituted pyrimidyl, and optionally substituted thiazolyl; $R^1$ and $R^2$ are independently selected from hydrogen, alkyl, halolalkyl, alkoxy, halogen; $R^3$ is a valence bond or is selected from hydrogen and alkyl; X is a valence bond or is selected from alkylene, alkenylen, and alkynylene; and Z is selected from (a) COM, (b) CH=N—O—A—COM, (c) $CH_2$—O—N=A—COM wherein A is selected from alkylene and cycloalkylene, and M is selected from (a) a pharmaceutically acceptable metabolically cleavable group, (b) —$OR^6$, (c) —$NR^7R^8$, (d)—$NR^6SO_2R^9$, (e)-NH-Tetrazolyl, and (f) glycinyl inhibit leukotriene biosynthesis and are useful in the treatment of allergic and inflammatory disease states. Also disclosed are leukotriene biosynthesis inhibiting compositions and a method of inhibiting leukotriene biosynthesis.

16 Claims, No Drawings

SYMMETRICAL BIS-HETEROARYL-METHOXY-PHENYLALKYL CARBOXYLATES AS INHIBITORS OF LEUKOTRIENE BIOSYNTHESIS

CROSS REFERENCE TO RELATED APPLICATIONS

This application claims benefit of U.S. Provisional Application No. 60/004,706, filed Oct. 3, 1995.

TECHNICAL FIELD

This invention relates to compounds having activity to inhibit leukotriene biosynthesis, to pharmaceutical compositions comprising these compounds, and to a medical method of treatment. More particularly, this invention concerns a class of symmetrical bis-heteroarylmethoxyphenylalkyl carboxylate compounds which inhibit leukotriene biosynthesis, to pharmaceutical compositions comprising these compounds and to a method of inhibiting leukotriene biosynthesis.

BACKGROUND OF THE INVENTION

The leukotrienes are extremely potent substances which produce a wide variety of biological effects, often even when present only in nanomolar to picomalar concentrations. Leukotrienes are important pathological mediators in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

Compounds which prevent leukotriene biosynthesis are thus useful in the treatment of disease states such as those listed above in which the leukotrienes play an important pathophysiological role.

U.S. Pat. No. 5,358,955 (Oct. 25,1994) discloses aryl and heteroarylmethoxyphenyl compounds which inhibit leukotriene biosynthesis.

U.S. Pat. No. 4,970,215 (Nov. 13, 1990) discloses quinolylmethoxyphenyl acetic acid derivatives which inhibit leukotriene biosynthesis.

U.S. Pat. No. 5,512,581 discloses iminoxycarboxylate derivatives which inhibit leukotriene biosynthesis. U.S. Pat. No. 5,326,883 (Jul. 5, 1994) discloses oxime ether derivatives having lipoxygenase inhibitory activity.

European Patent Application Number 349 062 (Jan. 3, 1990) discloses quinolylmethoxyphenyl alkanoic acid derivatives which inhibit leukotriene biosynthesis.

PCT Application Number WO 94/27968 (Dec. 8, 1994) discloses quinoline derivatives as leukotriene antagonists.

Prasit, et al., *Bioorganic and Medicinal Chemistry Letters*, 1 (11), 645 (1991) describe ((4-(4-chlorophenyl)-1-(4-(2-quinolylmethoxy)phenyl)butyl)thio)acetic acid as an orally active leukotriene biosynthesis inhibitor, and Musser and Kraft, *Journal of Medicinal Chemistry*, 35 (14), 1, (1992) review quinoline containing leukotriene biosynthesis inhibitors.

SUMMARY OF THE INVENTION

In its principal embodiment, the present invention provides a class of novel symmetrical bis-heteroarylmethoxyphenylalkyl carboxylate compounds and their derivatives and pharmaceutically acceptable salts. The compounds have the formula:

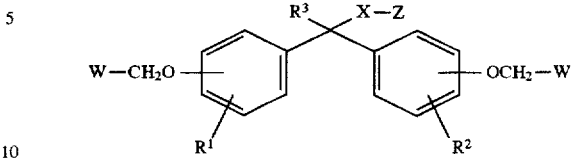

wherein W is the same at each occurrence and is selected from the group consisting of (a) quinolyl; (b) quinolyl substituted with a substituent selected from the group consisting of (b-1) halogen, (b-2) alkyl of one to six carbon atoms, (b-3) phenyl, (b-4) phenyl substituted with a substituent selected from the group consisting of (b-4-a) halogen, (b-4b) alkyl of one to six carbon atoms, (b-4-c) haloalkyl of one to six carbon atoms, and (b-4-d) alkoxy of one to six carbon atoms, (b-5) pyridyl, and (b-6) pyridyl substituted with a substituent selected from the group consisting of (b-6-a) halogen, (b-6-b) alkyl of one to six carbon atoms, and (b-6-c) alkoxy of one to six carbon atoms; (c) benzothiazolyl; (d) benzothiazolyl substituted with a substituent selected from the group consisting of (d-1) halogen, (d-2) alkyl ol one to six carbon atoms, (d-3) phenyl, (d-4) phenyl substituted with a substituent selected from the group consisting of (d-4-a) halogen, (d-4-b) alkyl of one to six carbon atoms, (d-4-c) haloalkyl of one to six carbon atoms, and (d-4-d) alkoxy of one to six carbon atoms, (d-5) pyridyl, and (d-6) pyridyl substituted with a substituent selected from the group consisting of (d-6-a) halogen, (d-6-b) alkyl of one to six carbon atoms, and (d-6-c) alkoxy of one to six carbon atoms; (e) benzoxazolyl; (f) benzoxazolyl substituted with a substituent selected from the group consisting of (f-1) halogen, (f-2) alkyl of one to six carbon atoms, (f-3) phenyl, (f-4) phenyl substituted with a substituent selected from the group consisting of (f-4-a) halogen, (f-4-b) alkyl of one to six carbon atoms, (f-4-c) haloalkyl of one to six carbon atoms, and (f-4-d) alkoxy of one to six carbon atoms, (f-5) pyridyl, and (f-6) pyridyl substituted with a substituent selected from the group consisting of (f-6-a) halogen, (f-6-b) alkyl of one to six carbon atoms, and (f-6-c) alkoxy of one to six carbon atoms; (g) benzimidazolyl; (h) benzimidazolyl substituted with a substituent selected from the group consisting of (h-1) halogen, (h-2) alkyl of one to six carbon atoms, (h-3) phenyl, (h-4) phenyl substituted with a substituent selected from the group consisting of (h-4-a) halogen, (h-4-b) alkyl of one to six carbon atoms, (h-4-c) haloalkyl of one to six carbon atoms, and (h-4-d) alkoxy of one to six carbon atoms, (h-5) pyridyl, and (h-6) pyridyl substituted with a substituent selected from the group consisting of (h-6-a) halogen, (h-6-b) alkyl of one to six carbon atoms, and (h-6-c) alkoxy of one to six carbon atoms; (i) quinoxalyl; (j) quinoxalyl substituted with a substituent selected from the group consisting of (j-1) halogen, (j-2) alkyl of one to six carbon atoms, (j-3) phenyl, (j-4) phenyl substituted with a substituent selected from the group consisting of (j-4-a) halogen, (j-4-b) alkyl of one to six carbon atoms, (j-4-c) haloalkyl of one to six carbon atoms, and (j-4-d) alkoxy of one to six carbon atoms, (j-5) pyridyl, and (j-6) pyridyl substituted with a substituent selected from the group consisting of (j-6-a) halogen, (j-6-b) alkyl of one to six carbon atoms, and (j-6-c) alkoxy of one to six carbon atoms; (k) pyridyl; (l) pyridyl substituted with a substituent selected from the group consisting of (1-1) phenyl, (1-2) phenyl substituted with a substituent selected from the group consisting of (1-2-a) halogen, (1-2-b) alkyl of one to six carbon atoms, (1-2-c) haloalkyl of one to six carbon atoms, and (1-2-d) alkoxy of one to six carbon atoms, (1-3) pyridyl, and (1-4) pyridyl substituted with a substituent selected from the group consisting of (1-4-a) halogen, (1-4-b) alkyl of one to six carbon atoms, and (1-4-c) alkoxy of one to six carbon atoms; (m) pyrimidyl; (n) pyrimidyl substituted with a substituent selected from the group consisting of (n-1) phenyl, (n-2) phenyl substituted with a substituent selected from the group consisting of (n-2-a) halogen, (n-2-b) alkyl of one to six carbon atoms, (n-2-c) haloalkyl of one to six carbon atoms, and (n-2-d) alkoxy of one to six carbon atoms, (n-3) pyridyl, and (n-4) pyridyl substituted with a substituent selected from the group consisting of (n-4-a) halogen, (n-4-b) alkyl of one to six carbon atoms, and (n-4-c) alkoxy of one to six carbon atoms; (o) thiazolyl, and (p) thiazolyl substituted with a substituent selected from the group consisting of (p-1) phenyl, (p-2) phenyl substituted with a substituent selected from the group consisting of (p-2-a) halogen, (p-2-b) alkyl of one to six carbon atoms, (p-2-c) haloalkyl of one to six carbon atoms, and (p-2-d) alkoxy of one to six carbon atoms, (p-3) pyridyl, and (p-4) pyridyl substituted with a substituent selected from the group consisting of (p-4-a) halogen, (p-4-b) alkyl of one to six carbon atoms, and (p-4-c) alkoxy of one o six carbon atoms.

$R^1$ and $R^2$ are independently selected from the group consisting of (a) hydrogen, (b) alkyl of one to six carbon atoms, (c) halolalkyl of one to six carbon atoms, (d) alkoxy of one to six carbon atoms, and (e) halogen.

$R^3$ is selected from the group consisting of (a) hydrogen and (b) alkyl of one six carbon atoms.

X is absent or is selected from the group consisting of (a) alkylene of one to six carbon atoms, (b) alkenylene of one to six carbon atoms, and (c) alkynylene of one to six carbon atoms.

Z is selected from the group consisting of (a) COM, (b) CH=N—O—A—COM, (c) CH$_2$—O—N=A—COM, and (d) OR$^3$ where R$^3$ is hydrogen or alkyl of one to six carbon atoms.

A is selected from the group consisting of (a) alkylene of one to six carbon atoms, and (b) cycloalkylene of three to eight carbon atoms.

M is selected from the group consisting of (a) a pharmaceutically acceptable metabolically cleavable group, (b) —OR$^3$ where R$^3$ is selected from the group consisting of hydrogen and alkyl of one to six carbon atoms, and (c)—NR$^7$R$^8$ where R$^7$ and R$^8$ are independently selected from the group consisting of hydrogen, alkyl of one to six carbon atoms, hydroxy, and alkoxy of one to six carbon atoms, or R$^7$ and R$^8$ taken together define a five- to eight-membered ring, with the proviso that R$^7$ and R$^8$ may not simultaneously be hydroxyl, (d) —NR$^3$SO$_2$R$^9$ wherein R$^3$ is as defined above and R$^9$ is alkyl of one to six carbon atoms, (e)-NH-tetrazolyl, and (f) glycinyl.

The present invention also provides pharmaceutical compositions which comprise a therapeutically effective amount of compound as defined above in combination with a pharmaceutically acceptable carrier.

The invention further relates to a method of inhibiting leukotriene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The term alkenyl as used herein refers to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a divalent group derived from a straight or branched chain saturated hydrocarbon by the removal of two hydrogen atoms, for example —CH$_2$—, —CH$_2$CH$_2$—, —CH(CH$_3$)CH$_2$—and the like.

The term alkenylene denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term alkynylene refers to a divalent group derived by the removal of two hydrogen atoms from a straight or branched chain acyclic hydrocarbon group containing at least one carbon-carbon triple bond. Examples of alkynylene include —CH≡CH—, —C≡CH—CH$_2$—, —CH≡CH—CH(CH$_3$)—, and the like.

The term aryl as used herein refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

The term cycloalkyl as used herein refers to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The term haloalkyl denotes an alkyl group, as defined above, having one, two, or three halogen atoms attached thereto and is exemplified by such groups as chloromethyl, bromoethyl, trifluoromethyl, and the like.

As used throughout this specification and the appended claims, the term "metabolically cleavable group" denotes a moiety which is readily cleaved in vivo from the compound bearing it, which compound after cleavage remains or becomes pharmacologically active. Metabolically cleavable groups form a class of groups reactive with the carboxyl group of the compounds of this invention (where M is —OH) well known to practitioners of the art. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs of other leukotriene biosynthesis inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

In those instances where M=OH, the compounds of the present invention are capable of forming base addition salts. In such instances, the term "pharmaceutically acceptable salts" refers to the relatively nontoxic inorganic and organic base addition salts of compounds of the present invention. These salts can be prepared in situ during the final isolation and purification of the compounds, or by separately reacting the purified carboxyl compound with a suitable base such as the hydroxide, carbonate, or bicarbonate of a pharmaceutically acceptable metal cation or with ammonia, or an organic primary, secondary, or tertiary amine of sufficient basicity to form a salt with the carboxyl functional group of the compounds of this invention.

Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. (See, for example, S. M. Berge, et al., *J. Pharmaceutical Sciences*, 1977, 66: 1–19, which is incorporated herein by reference).

Similarly, in those instances where the compounds of the present invention possess a heterocyclic ring moiety containing a basic nitrogen atom, the compounds are capable of forming acid addition salts. In such cases, the term "pharmaceutically acceptable salts" also refers to the nontoxic inorganic and organic acid addition salts of compounds of the present invention. These salts can be prepared in situ during the final isolation and purification of the compounds, or by separately reacting the purified compound in its free-base form with a suitable inorganic or organic acid and isolating the salt thus formed. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphtlhalenesulfonate, nicotinate, nitrate, oleate, oxalate, palmitate, parnoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. (See, for example, S. M. Berge, et al., *J. Pharmaceutical Sciences*, 1977, 66: 1–19), which is incorporated herein by reference). Said pharmaceutically acceptable acid and base addition salts are also contemplated as falling within the scope of the present invention.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

Examples of compounds contemplated as falling within the scope of the present invention include, but are not limited to:

4,4-bis(4-(2-quinolylmethoxy)phenyl)pentanoic acid, 4,4-bis(4-(2-quinolylmethyl)phenyl)pentanoic acid methyl ester, 4,4-bis(4-(2-quinolylmethoxy)phenyl)pentanoic acid sodium salt, 4,4-bis(4-(2-quinolylmethoxy)phenyl) pentanoic acid magnesium salt, 4,4-bis(4-(2-quinolylmethoxy)phenyl)pentan-1-ol,

[4,4-bis(4-(2-quinolylmethoxy)phenyl)pent-1-yl] iminoxyacetic acid,

[4,4-bis(4-(2-quinolylmethoxy)phenyl)pent-1-yl]-2-iminoxypropionic acid,

[4,4-bis(4-(2-quinolylmethoxy)phenyl)pent-1-yl]-2-iminoxypropionic acid, methyl ester,

[4,4-bis(4-(2-quinolylmethoxy)phenyl)pent-1-yl] oximinoacetic acid, 4,4-bis(4-(2-benzothiazoylmet oxy)phenyl)pentanoic acid, 4,4-bis(4-(2-benzothiazoylmethoxy)phenyl)pentanoic acid sodium salt, 4,4-bis(4-(7-chloro-2-quinolylmethoxy)phenyl)pentanoic acid, 4,4-bis(4-(6-fluoro-2-quinolylmethoxy)phenyl)pentanoic acid sodium salt, 4,4-bis(4-(6-fluoro-2-quinolylmethoxy)phenyl)pentanoic acid, 2,2-bis(4-(2-quinolylmethoxy)phenyl)propionic acid, 3,3-bis(4-(2-quinolylmethoxy)phenyl)butanoic acid, 5,5-bis(4-(2-quinolylmethoxy)phenyl)hexanoic acid, 5,5-bis(4-(2-quinolylmethoxy)phenyl)hexanoic acid sodium salt, 4,4-bis-(4-(2-pyridylmethoxy)phenyl)pentanoic acid sodium salt, 4,4-bis-(4-(2-pyridylmethoxy)phenyl)pentanoic acid, 4,4-bis-(4-(2-quinoxylmethoxy)phenyl)pentanoic acid sodium salt, 4,4-bis(4-(1-methyl-2-benzimidazolylmethoxy)phenyl) pentanoic acid, 4,4-bis(4-(1-methyl-2-benzimidazolylmethoxy)phenyl) pentanoic acid sodium salt, 4,4-bis(3-chloro-4-(2-quinolylmethoxy)phenyl)pentanoic acid, 4,4-bis(3-chloro-4-(2-quinolylmethoxy)phenyl)pentanoic acid methyl ester, 4,4-bis(3-chloro-4-(2-quinolylmethoxy)phenyl)pentanoic acid sodium salt,

[4,4-bis(3-chloro-4-(2-quinolylmethoxy)phenyl)pent-1-yl]-2-iminoxypropionic acid sodium salt, 4,4-bis(3-chloro-4-(2-quinolylmethoxy)phenyl)pentan-1-ol,

[4,4-bis(3-chloro-4-(2-quinolylmethoxy)phenyl)pent-1-yl]-2-irminoxypropionic acid, 4,4-bis(4-(2-quinolylmethoxy)phenyl)pentanoic acid N,N-diethylhydroxylamine ester, 2,2-bis(4-(2-quinolylmethoxy)phenyl)butyric acid, 1,1-bis(4-(2-quinolylmethoxy)phenyl)ethanol, 2,2-dimethyl-3,3-bis(4-(2-quinolylmethoxy)phenyl) propionic acid sodium salt, 2,2-dimethyl-3,3-bis(4-(2-quinolylmethoxy)phenyl) propionic acid methyl ester, 2,2-dimethyl-3,3-bis(4-(2-quinolylmethoxy)phenyl) propionic acid,

[2,2-dimethyl-3,3-bis(4-(2-quinolylmethoxy)phenyl) prop-1-yl]oximinoacetic acid sodium salt, 2,2-dimethyl-3,3-bis(4-(2-quinolylmethoxy)phenyl) propan-1-ol,

[2,2-dimethyl-3,3-bis(4-(2-quinolylmethoxy)phenyl) prop-1-yl]oximinoacetic acid, 2,2-dimethyl-3,3-bis(4-(2-quinolylmethoxy)phenyl)-1-propylirninoxyacetic acid, 2,2-bis(4-(2-quinolymethoxy)phenyl)acetic acid, 2,2-bis(4-(6-fluoro-2-quinolymethoxy)phenyl)acetic acid, 2,2-bis(4-(2-quinolylmethoxy)phenyl)eth-1-yloximinoacetic acid, 2,2-bis(4-(2-quinolymethoxy)phenyl)acetic acid methyl ester, 2,2-bis(4-(2-quinolylmethoxy)phenyl)eth-1-yloxirninoacetic acid sodium salt, 3,3-bis(4-(2-quinolylmethoxy)phenyl)propionic acid, 3,3-bis(4-(2-quinolylmethoxy)phenyl)propionic acid sodium salt, 4,4-bis(4-(2-quinolylmethoxy)phenyl)acetic acid-N-carboxymethyl amide,

[3,3-bis-(2-quinolylmethoxyphenyl)but-1-yl]-2-iminoxypropionic acid, 3,3-bis(4-(2-quinolylmethoxy)phenyl)butan-1-ol, 4,4-bis(4-(2-quinolylmethoxy)phenyl)-4-hydroxy-2-butynoic acid, 4,4-bis(2-quinolylmethoxy)phenyl)-4-hydroxy-2-butynoic acid methyl ester,

[5,5-bis (4-(2-quinolylmethoxy)phenyl)-5-hydroxy-3-pentyn-1-yl]-2-iminoxypropionic acid sodium salt,

[5,5-bis(4-(2-quinolylmethoxy)phenyl)-5-hydroxy-3-pentyn-1-yl]-2-iminoxypropionic acid, 4,4-bis(4-(2-benzoxazolylmethoxy)phenyl)pentanoic acid, 4,4-bis(4-(2-pyrimidylmethoxy)phenyl)pentanoic acid, 4,4-bis(4-(4-phenyl-2-thiazolylmethoxy)phenyl) pentanoic acid, 4,4-bis(4-(4-(pyrid-2-yl)-2-thiazolylmethoxy)phenyl) pentanoic acid, 4,4-bis(4-(6-phenyl-2-pyridylmethoxy)phenyl)pentanoic acid, 4,4-bis(4-(5-phenyl-2-pyridylmethoxy)phenyl)pentanoic acid, 4,4-bis(4-(6-(pyrid-2-yl)-2-pyridylmethoxy)phenyl) pentanoic acid, and 4,4-bis(4-(4-phenyl-2-pyrimidylmethoxy)phenyl) pentanoic acid.

Preferred compounds of the present invention have the structure defined above wherein Z is selected from the group consisting of (a) COM, (b) CH=N—O—A—COM, (c) CH$_2$—O—N=A—COM, and (d) OH wherein A is alkylene of one to six carbon atoms, and M is -OH.

More preferred compounds of the present invention have the structure defined immediately above wherein W is selected from the group consisting of (a) quinolyl; (b) quinolyl substituted with a substituent selected from the group consisting of (b-1) halogen, (b-2) alkyl of one to six carbon atoms, (b-3) phenyl, (b-4) phenyl substituted with a substituent selected from the group consisting of (b-4-a) halogen, (b-4-b) alkyl of one to six carbon atoms, (b-4-c) haloalkyl of one to six carbon atoms, and (b-4-d) alkoxy of one to six carbon atoms, (b-5) pyridyl, and (b-6) pyridyl substituted with a substituent selected from the group consisting of (b-6-a) halogen, (b-6-b) alkyl of one to six carbon atoms, and (b-6-c) alkoxy of one to six carbon atoms; (c) benzothiazolyl; and (d) benzothiazolyl substituted with a substituent selected from the group consisting of (d-1) halogen, (d-2) alkyl of one to six carbon atoms, (d-3) phenyl, (d-4) phenyl substituted with a substituent selected from the group consisting of (d-4-a) halogen, (d-4-b) alkyl of one to six carbon atoms, (d-4-c) haloalkyl of one to six carbon atoms, and (d-4-d) alkoxy of one to six carbon atoms, (d-5) pyridyl, and (d-6) pyridyl substituted with a substituent selected from the group consisting of (d-6-a) halogen, (d-6-b) alkyl of one to six carbon atoms, and (d-6-c) alkoxy of one to six carbon atoms.

Still more preferred compounds have the structure defined immediately above wherein X is alkylene of one to six carbon atoms, and Z is COOH.

The most preferred compounds of the present invention have the structure defined immediately above wherein W is the same at each occurrence and is selected from the group consisting of (a) quinolyl; and (b) quinolyl substituted with a substituent selected from the group consisting of (b-1) halogen, (b-2) alkyl of one to six carbon atoms, (b-3) phenyl, (b-4) phenyl substituted with a substituent selected from the group consisting of (b-4-a) halogen, (b-4-b) alkyl of one to six carbon atoms, (b-4-c) haloalkyl of one to six carbon atoms, and (b-4-d) alkoxy of one to six carbon atoms, (b-5) pyridyl, and (b-6) pyridyl substituted with a substituent selected from the group consisting of (b-6-a) halogen, (b-6-b) alkyl of one to six carbon atoms, and (b-6-c) alkoxy of one to six carbon atoms.

Compounds representative of the most preferred embodiment include, but are not limited to 4,4-bis(4-(2-quinolylmethoxy)phenyl)pentanoic acid, 4,4-bis(4-(2-quinolylmethoxy)phenyl)pentanoic acid sodium salt, 4,4-bis(4-(2-quinolylmethoxy)phenyl) pentanoic acid magnesium salt, 4,4-bis(4-(2-benzothiazoylmethoxy)phenyl)pentanoic acid, 4,4-bis(4-(2-benzothiazoylmethoxy)phenyl)pentanoic acid sodium salt, 4,4-bis(4-(7-chloro-2-quinolylmethoxy)phenyl)pentanoic acid, 4,4-bis(4-(7-fluoro-2-quinolylmethoxy)phenyl)pentanoic acid sodium salt, 2,2-bis(4-(2-quinolylmethoxy)phenyl)propionic acid, 3,3-bis(4-(2-quinolylmethoxy)phenyl)butanoic acid, 5,5-bis(4-(2-quinolylmethoxy)phenyl)hexanoic acid, 5,5-bis(4-(2-quinolylmethoxy)phenyl)hexanoic acid sodium salt, 4,4-bis(3-chloro-4-(2-quinolylmethoxy)phenyl)pentanoic acid, 4,4-bis(3-chloro-4-(2-quinolylmethoxy)phenyl)pentanoic acid sodium salt, 2,2-bis(4-(2-quinolylmethoxy)phenyl)butyric acid, 2,2-dimethyl-3,3-bis(4-(2-quinolylmethoxy)phenyl) propionic acid sodium salt, 2,2-bis(4-(2-quinolymethoxy)phenyl)acetic acid, 2,2-bis(4-(6-fluoro-2-quinolymethoxy)phenyl)acetic acid, 2,2-bis(4-(2-quinolylmethoxy)phenyl)propionic acid, and 2,2-bis(4-(2-quinolylmethoxy)phenyl)propionic acid sodium salt.

Lipoxygenase Inhibition Determination

Inhibition of leukotriene biosynthesis was evaluated in vitro using an assay involving calcium ionophore-induced $LTB_4$ expressed in human polymorphornuclear leukocytes (PMNL). Human PMNL isolated from heparinized (20 USP units/mL) venous blood (25 mL) obtained from healthy volunteers was layered over an equal volume of Ficoll-Hypaque Mono-Poly Resolving Medium (ICN Flow, Costa Mesa, Calif.) and centrifugated at 400×g for 40 minutes at 20° C. The PMNL was collected, erythrocytes lysed and washed 2× and suspended at $1.0 \times 10^7$ cells/mL in Earle's balanced salt solution with 17 mM Earle's HEPES. Aliquots of the cell suspension were preincubated with test compounds dissolved in DMSO (final concentration <2%) for 15 minutes and stimulated with calcium ionophore (final concentration 8.3, μM) for 10 minutes at 37° C. Incubations were stopped with the addition of two volumes of ice-cold methanol followed by centrifuging the cell suspensions at 4° C. for 10 minutes at ~450×g. The amount of $LTB_4$ in the methanol extract was analyzed by enzyme-linked immunoassay or by HPLC analysis.

The compounds of this invention inhibit leukotriene biosynthesis as shown by the data for representative examples in Table 1.

TABLE 1

In Vitro Inhibitory Potencies Against 5-Lipoxygenase From Stimulated $LTB_4$ Formation in Human Polymorphonuclear Leukocytes

| Example | $IC_{50}$ (μM) |
|---|---|
| 1 | 0.040 |
| 2 | 0.069 |
| 5 | 0.030 |
| 6 | 0.035 |
| 7 | 0.040 |
| 8 | 0.046 |
| 9 | 0.050 |
| 11 | 0.040 |
| 12 | 0.032 |
| 14 | 0.043 |
| 20 | 0.026 |
| 25 | 0.050 |
| 26 | 0.080 |
| 27 | 0.028 |
| 28 | 0.034 |
| 30 | 0.050 |
| 31 | 0.035 |
| 34 | 0.070 |
| 36 | 0.025 |
| 38 | 0.060 |

Inhibition of leukotriene biosynthesis in vivo was evaluated using the Ionophore A32187-Induced Rat Plueral Inflammation Model. Pleural inflammation was induced in male rats following the method of Rao et al (Rao, T. S., Currie, J. L., Shaffer, A. F., Isakson, P. C.(1993) Evaluation of 5-lipoxygenase Inhibitors, Zileuton, A-78773 and ICI D-2138 in an Ionophore (A-23187) Induced Pleural Inflammation Model in the Rat, *Life Sciences*, 53: 147 (1993)). Rats were dosed with experimental compounds in 0.2% methocel one hour prior to the intrapleural injection of the calcium ionophore, A23187.The rats where lightly anesthetized with Pentrane (Abbott Laboratories) and injected intrapleurally with 0.5 ml of 2% ethanol in injectable saline (Abbott Laboratories) containing 20 μg of A23187 (Cal BioChem-Novabiochem). Thirity minutes later the animals were euthanised and the pleural cavities lavaged with ice cold saline (Abbott Laboratories). The lavage fluid was then added to ice cold methanol (final methanol concentration 30%) to lyse cells and precipitate protein. Eicosadnoids were determrined by enzyme immunoassay by standard methods.

TABLE 2

In Vivo Leukotriene Inhibition in Rat Pleural Inflammation

| Example | % Inhibition at 3 mg/kg |
|---|---|
| 2 | 53% |
| 11 | 42% |
| 14 | 32% |
| 24 | 38% |
| 26 | 50% |
| 27 | 42% |
| 34 | 30% |
| 38 | 40% |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills. powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethlylene sorbitol ,and sorbitan esters, microcrystalline cellulose, aluminum metahydroxide, bentonite, aparagar, and tragacanth, and mixtures thereof.

Compositions for rectal or vaginal administration are preferably suppositories which can be prepared by mixing the compounds of this invention with suitable non irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33, et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g., two to four separate doses per day.

Preparation Of Compounds Of This Invention

In general, the compounds of this invention are synthesized by reaction schemes 1-3 as illustrated below. The preparation of compounds of this invention wherein Z is $CO_2R^6$, wherein $R^6$ is H or alkyl is outlined in Scheme 1. Reaction of two equivalents of phenol with the requisite carbonyl (keto or aldehyde) ester in the presence of acid gives adducts of formula I (see U.S. Pat. No. 2,933,520). Intermediates of formula I wherein $R^6$ is H are esterified, for example by reaction with an alcohol in the presence of acid, to give an ester of formula II, which is then reacted with a heteroarylmethyl halide of formula W—$CH_2X$ where X is Cl, Br, or I, and W is defined above in the presence of a suitable base such as $K_2CO_3$ to provide the desired compound III in which $R^6$ is alkyl. Hydrolysis of the ester, for example using aqueous alkali, provides compounds of formula IV wherein $R^6$ is H.

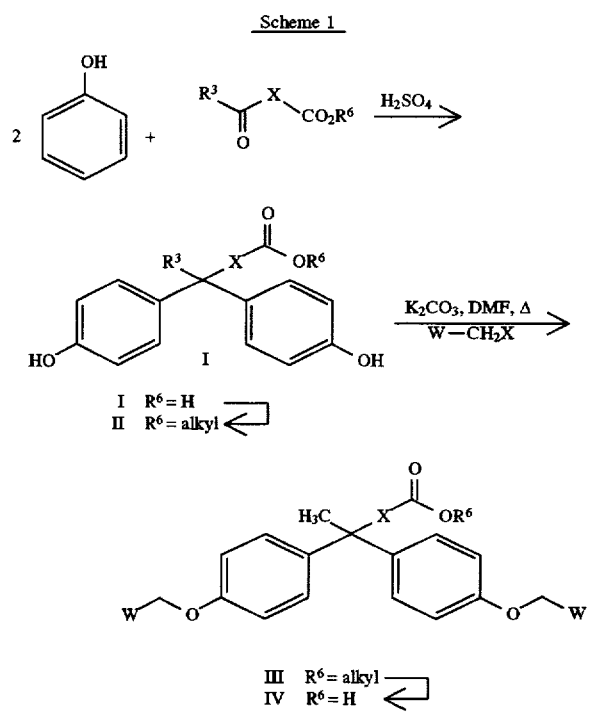

A general procedure for the synthesis of compounds of this invention wherein Z is $OR^4$ or CH=N—O—A—COM is described in Scheme 2. Reduction of ester III, for example using lithium aluminum hydride or sodium borohydride, or acid IV, for example using lithium aluminum hydride or using sodium borohydride to reduce the mixed anhydride made from the acid and ethyl chloroformate, provides alcohol V. Compounds of this invention wherein $R^4$ is alkyl are then prepared from V using methods well-known in the art such as reaction with alkyl iodide in the presence of base. Alcohol V is converted to compounds of this invention wherein CH=N—O—A—COM by oxidation to the aldehyde, for example using Swern oxidation conditions (Swern, et al., *J. Org. Chem.*, 1978, 43, 2480), followed by reaction with the requisite hydroxylamine derivative $H_2N$—O—A—COM.

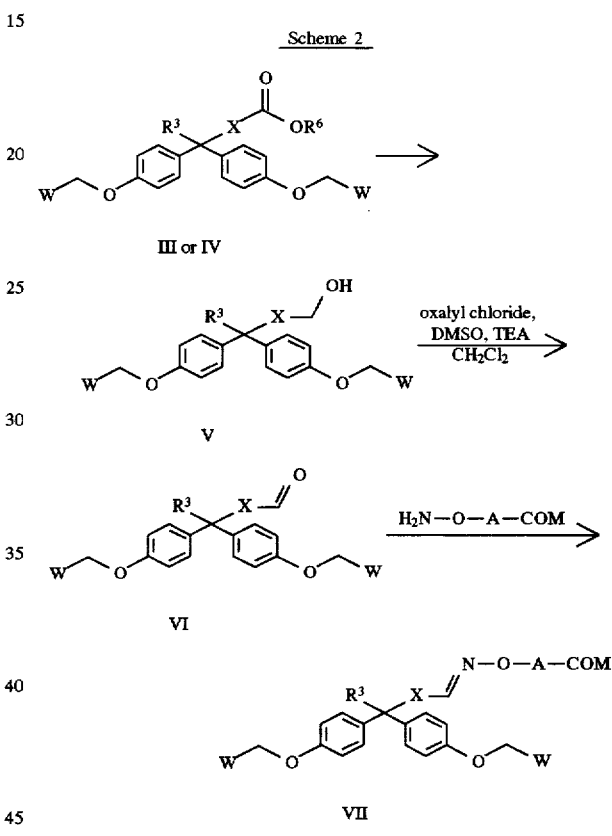

The preparation of compound of this invention wherein Z is $CH_2$—O—N=A—COM is described in Scheme 3. The hydroxy intermediate V, prepared in Scheme 2 above, is converted to hydroxylamine derivative VIII by known methods such as coupling with N-hydroxyphthalimide under Mitsunobu conditions (triphenyl-phosphine, diethyl or diisopropylazodicarboxylate; see Mitsunobu, O., *Synthesis*, 1981, 1), followed by treatment with hydrazine. The hydroxylamine derivative VIII is then reacted with the requisite carbonyl unit, O=A—COM to provide the compounds of this invention represented by the general structure IX.

Scheme 3

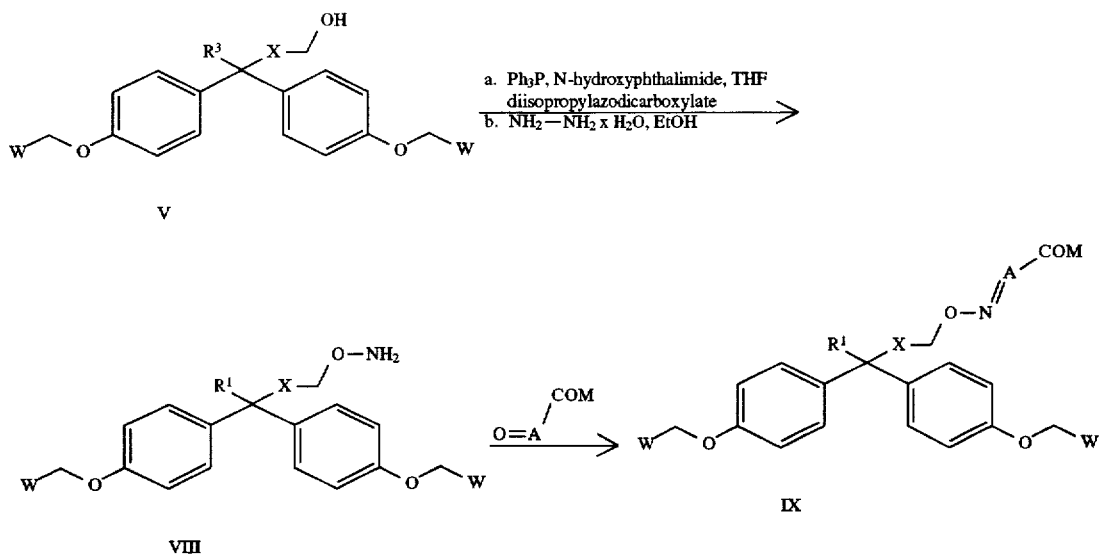

The foregoing may be better understood by reference to the following examples which are provided for illustration and are not intended to limit the scope of the invention as it is defined by the appended claims.

EXAMPLE 1

Preparation of 4,4-bis(4-(2-quinolylmethoxy) phenyl)pentanoic acid

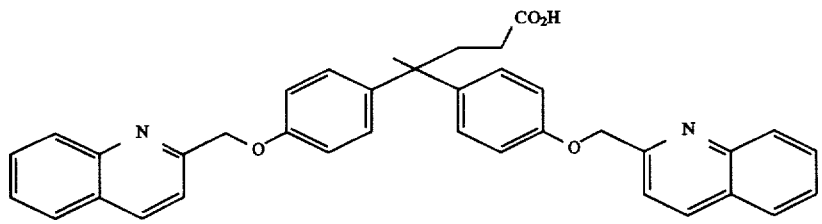

Step 1: 4,4-bis(4-hydroxyphenyl)pentanoic acid methyl ester

To a solution in methanol (120 mL) of 4,4-bis(4-hydroxyphenyl)pentanoic acid (Aldrich Chemical Co., 12 g, 42 mmol) was added concentrated $H_2SO_4$ (0.5 mL) and the mixture was heated to reflux for 3 hours. After cooling to room temperature the mixture was concentrated in vacuo and dissolved in ether (300 mL). The organic layer was washed with saturated aqueous $NaHCO_3$ (2×150 mL) and brine, dried over $MgSO_4$, filtered, and concentrated in vacuo to provide a thick oil which was crystallized from ether/hexane to give 4,4-bis(4-hydroxyphenyl)pentanoic acid methyl ester as an off-white color solid (11.8 g, 94%), mp 130° C.

Step 2: 4,4-bis(4-(2-quinolylmethylyphenyl)pentanoic acid methyl ester

To a solution in dry DMF under $N_2$ of 4,4-bis(4-hydroxyphenyl)pentanoic acid methyl ester (6.0 g, 20 mmol), prepared as in step 1, was added powdered $K_2CO_3$ (11.0 g, 80 mmol) and the reaction was stirred for 10 minutes after which 2-chloromethylquinoline hydrochloride (8.5 g, 40 mmol) was added. The mixture was heated at 60° C. for 18 hours and then cooled to room temperature, diluted with EtOAc (200 mL), washed with water and brine, dried over $MgSO_4$, filtered and concentrated in vacuo to provide a residue which was purified by chromatography on silica gel (9:1 $CH_2Cl_2$/EtOAc) to provide 10.8 (92%) of 4,4-bis(4-(2-quinolylmethyl)phenyl)-pentanoic acid methyl ester.

Step 3: 4,4-bis(4-(2-quinolylmethoxy)phenyl)pentanoic acid

To a solution in 1:1 dioxane/methanol (100 mL) of 4,4-bis(4-(2-quinolylmethyl)phenyl)pentanoic acid methyl ester(3.3 g, 5.7 mmol), prepared as in step 2, was added aqueous 1N NaOH (10 mL) and the mixture was heated at reflux for 3 hours, cooled to room temperature, concentrated in vacuo, diluted with water and neutralized with 10% aqueous citric acid. The solid precipitate was collected by filtration, dried in vacuo, and purified by chromatography on silica gel (9:1 $CH_2Cl_2$/EtOAc, followed by 20:1 $CH_2Cl_2$/$CH_3OH$) to provide 2.53 g (70%) of the desired product. Crystallization from methylene chloride-hexanes gave 4,4-bis (4-(2-quinolylmethoxy)phenyl)pentanoic acid: mp 105°–106° C.; $^1H$ NMR (300 MHz, DMSO-$d_6$) d 1.50 (s, 3H), 1.95 (m, 2H), 2.27 (m, 2H), 5.34 (s, 4H), 6.98 (d, 4H, J=8 Hz), 7.10 (d, 4H, J=8 Hz), 7.65 (m, 4H), 7.80 (m, 2H), 8.00 (m, 4H), 8.42 (d, 2H, J=9 Hz), 12.00 (s, 1H); MS (DCI—$NH_3$) m/e 569 (M+H)$^+$. Anal. Calc'd. for $C_{37}H_{32}N_2O_4$: C, 78.15; H, 5.67; N, 4.93. Found: C, 77.52; H, 5.88; N, 4.60.

EXAMPLE 2

Preparation of 4,4-bis(4-(2-quinolylmethoxy) phenyl)pentanoic acid sodium salt

To a solution in dioxane (10 mL) and methanol (10 mL) of 4,4-bis (4-(2-quinolylmethoxy)phenyl)pentanoic acid (320 mg, 0.56 mmol), prepared as in step 1, was added aqueous 1N sodium hydroxide (0.55 ml, 0.55 mmol). The mixture was then concentrated in vacuo. The product was crystallized by dissolving in $CH_2Cl_2$ and precipitation by dropwise addition of a mixture of ethyl acetate-ethyl ether (1:2): $^1H$ NMR (300 MHz, DMSO—$d_6$) d 1.47 (s, 3H), 1.63 (m, 2H), 2.18 (m, 2H), 5.31 (s, 4H), 6.95 (d, 4H, J=9 Hz), 7.08 (d, 4H, J=9 Hz), 7.64 (m, 4H), 7.78 (m, 2H), 8.00 (m, 4H), 8.40 (d, 2H, J=8 Hz); MS (FAB+) m/e 591 (M+H)$^+$; (FAB$^-$) 589 (M−H)$^-$. Anal. Calc'd. for $C_{37}H_{31}N_2O_4Na.0.25$ $H_2O$:C, 74.67; H, 5.34; N, 4.71; Found: C, 74.57; H, 5.32; N, 4.52.

EXAMPLE 3

Preparation of 4,4-bis(4-(2-quinolylmethoxy) phenyl)pentanoic acid magnesium salt To a stirred room temperature THF solution of 4,4-bis(4-(2-quinolyl-methoxy)phenyl)pentanoic acid (0.6 g, 1.06 mmol), prepared as in Example 1, was added MgO (0.021 g, 0.528 mmol). Water was added until the mixture became homogeneous. The reaction was allowed to stir for 24 hours. The solvent was removed in vacuo and the residue triturated with hexanes. The precipitate was vacuum filtered and washed with hexanes. The solid was dried in vacuo at 55° C. for 48 hours to give 0.510 g (83%) of 4,4-bis(4-(2-quinolylmethoxy)phenyl)pentanoic acid magnesium salt as a cream-colored powder: mp 96°–110° C.; $^1H$ NMR (300 MHz, DMSO-$d_6$) d 1.42 (s, 6H), 1.76 (m, 4H), 2.21 (m, 4H), 5.27 (s, 8H), 6.91 (d, 8H, J=7.5 Hz), 7.03 (d, 8H, J=7.5 Hz), 7.58 (m, 8H), 7.74 (t, 4H, J=7.5 Hz), 7.96 (m, 8H), 8.34 (m, 4H). Anal. Calc'd. for $C_{74}H_{62}N_4O_8Mg.1.50 H_2O$: C, 74.90; H, 5.52; N, 4.72. Found: C, 74.81; H, 5.64; N, 4.68.

EXAMPLE 4

Preparation of 4,4-bis(4-(2-quinolylmethoxy) phenyl)pentan-1-ol

To a mixture in THF (50 mL) of 4,4-bis(4-(2-quinolylmethoxy)phenyl)-pentanoic acid 2-quinolylmethyl ester (2.1 g, 3 mmol), prepared as in Example 1, and sodium borohydride (380 mg, 10 mmol) was added dropwise methanol at 50°–55° C. and the mixture was stirred for 30 minutes. The mixture was cooled to room temperature, poured into water (50 mL) and acidified to pH 4. The resulting mixture was extracted with ethyl acetate, dried over MgSO4, filtered, and concentrated in vacuo. The residue was purified by chromatography on silica gel (methylene chloride-ethyl acetate 3:1) to afford 1.46 g (88%) of 4,4-bis(4-(2-quinolylmethoxy)phenyl)pentan-1-ol: $^1H$ NMR (300 MHz, DMSO—$d_6$) d 1.18 (m, 2H), 1.48 (s, 3H), 2.00 (m, 2H), 3.34 (m, 2H), 4.34 (t, 1H, J=6 Hz), 5.30 (s, 4H), 6.96 (d, 4H, J=9 Hz), 7.09 (d, 4H, J=9 Hz), 7.64 (m, 4H), 7.79 (m, 2H), 8.00 (t, 4H, J=8 Hz), 8.41 (d, 2H, J=8 Hz); MS (DCI—$NH_3$) m/e 555 (M+H)$^+$. Anal. Calc'd. for $C_{37}H_{34}N_2O_3$. 0.5 $H_2O$: C, 78.84; H, 6.44; N, 4.97. Found: C, 78.67; H, 5.95; N, 4.70.

EXAMPLE 5

Preparation of [4,4-bis(4-(2-quinolylmethoxy) phenyl)pent-1-yl]iminoxyacetic acid

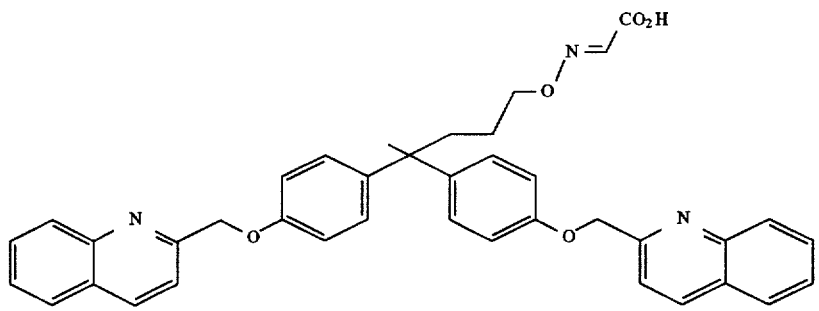

Step 1: N-phthaloyl-O-[4,4-bis(4-(2-quinolylmethoxy) phenyl)pent-1-yl]hydroxylamine To a solution in THF (35 mL) of 4,4-bis(4-(2-quinolylmethoxy)phenyl)-pentan-1-ol (1.11 g, 2 mmol), prepared as in Example 4, N-hydroxyphthalimide (326 mg, 2 mmol) and triphenylphosphine (786 mg, 3 mmol)was added a solution of DIAD (0.6 ml, 3 mmol) in THF (5 mL), and the resulting mixture was stirred at room temperature for 10 hours. The reaction mixture was concentrated in vacuo and purified by chromatography on silica gel (methylene chloride-ethyl acetate 12:1) to provide 1.33 g of N-phthaloyl-O-[4,4-bis(4-(2-quinolylmethoxy)phenyl) pent-1 -yl]hydroxylamine.

Step 2: O-[4,4-bis(4- (2-quinolylmethoxy)phenyl)pent-1 -yl]hydroxylamine

To a solution in dioxane (15 mL) and ethanol (15 mL) of the N-phthaloyl-O-[4,4-bis(4-(2-quinolylmethoxy)phenyl) pent-1-yl]hydroxylamine prepared in step 1 was added hydrazine hydrate (0.25 mL, 4 mmol) and the mixture was

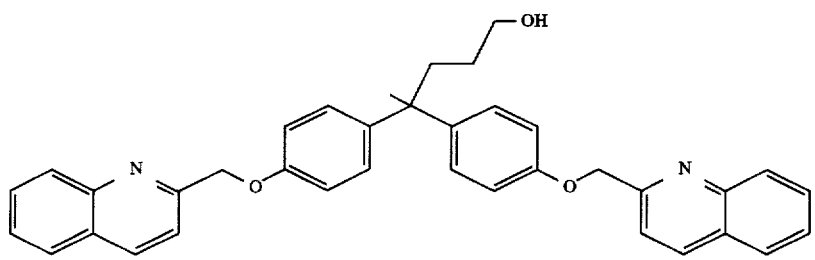

heated at reflux for 30 minutes. The mixture was then treated with aqueous 10% sodium carbonate (20 mL) and extracted with ethyl acetate. The organic extract was washed with water and brine, dried over MgSO$_4$, filtered, and concentrated in vacuo. The residue was purified by chromatography on silica gel (ethyl acetate) to afford 420 mg of O-|4,4-bis(4-(2-quinolylmethoxy)phenyl)pent-1-yl|hydroxylamine.

Step 3: |4,4-bis(4-(2-quinolylmethoxy)phenyl)pent-1 -yl| iminoxyacetic acid

A solution in dioxane (10 mL), methanol (5 mL) and water (2 mL) of O-|4,4-bis(4-(2-quinolylmethoxy)phenyl) pent-1-yl|hydroxylamine (114 mg, 0.2 mmol), prepared as in step 2, glyoxylic acid (19 mg, 0.2 mmol) and acetic acid (0.012 mL, 0.2 mmol) was stirred at ambient temperature for 16 hours. The mixture was then concentrated in vacuo and the residue was dissolved in ethyl acetate (50 mL). The resulting solution was washed with water and brine, dried over MgSO$_4$, filtered, and concentrated in vacuo. The residue was crystallized from methylene chloride-hexane to afford 108 mg (86%) of [4,4-bis(4-(2-quinolylmethoxy) phenyl)pent-1-yl]iminoxyacetic acid: mp 80°-82° C.; $^1$H NMR (300 MHz, DMSO—d$_6$) d 1.40 (m, 2H), 1.53 (s, 3H), 2.04 (m, 2H), 4.10 (t, 2H, J=7 Hz), 5.31 (s, 4H), 6.95 (d,4H J=9 Hz), 7.08 (d, 4H, J=9 Hz), 7.52 (s, 1H), 7.63 (m, 4H), 7.78 (m, 2H), 8.00 (m, 4H), 8.40 (d, 2H, J=8 Hz); MS (DCI—NH$_3$) m/e: 626 (M+H)$^+$. Anal. Calc'd. for C$_{39}$H$_{35}$N$_3$O$_5$: C, 74.86; H, 5.64; N, 6.72; Found: C, 74.89; H, 6.03; N, 6.42.

EXAMPLE 6

Preparation of [4,4-bis(4-(2-quinolylmethoxy) phenyl)pent-1-yl]-2-iminoxypropionic acid Step 1 : |4,4-bis(4-(2-quinolylmethoxy)phenyl)pent-1-yl|-2-iminoxypropionic acid methyl ester A mixture in dioxane (20 mL) and methanol (20 mL) of O-|4,4-bis(4-(2-quinolylmethoxy)phenyl)pent-1-yl| hydroxylamine (306 mg, 0.54 mmol), prepared as in Example 5, step 2, methyl pyruvate (0.055 mL, 0.55 mmol) and acetic acid (0.033 mL, 0.55 mmol) was stirred at room temperature for 12 hours. The mixture was then partitioned between aqueous 10% sodium bicarbonate and ethyl acetate. The ethyl acetate extract was washed with water and brine, dried over MgSO$_4$, filtered, and concentrated in vacuo. The residue was purified by chromatography on silica gel (methylene chloride-ethyl acetate 4:1) to afford 320 mg of |4,4-bis(4-(2-quinolyl-methoxy)phenyl)pent-1-yl|-2-iminoxypropionic acid methyl ester.

Step 2: [4,4-bis(4-(2-quinolylmethoxy)phenyl)pent-1-yl]-2-iminoxypropionic acid

The desired compound was prepared according to the method of Example 1, step 3, except substituting [4,4-bis (4-(2-quinolylmethoxy) phenyl)pent-1-yl]-2-iminoxypropionic acid methyl ester, prepared as in step 1, for 4,4-bis(4-(2-quinolylmethyl)phenyl)pentanoic acid methyl ester: mp 80°-82° C.; $^1$H NMR (300 MHz, DMSO—d$_6$) d 1.42 (m, 2H), 1.53 (s, 3H), 1.90 (s, 3H), 2.05 (m, 2H), 4.11 (t, 2H, J=7 Hz), 5.33 (s, 4H), 6.95 (d, 4H, J=9 Hz), 7.09 (d, 4H, J=9 Hz), 7.64 (m, 4H), 7.78 (m, 2H), 8.00 (m, 4H), 8.41 (d, 2H, J=8 Hz); MS (DCI—NH$_3$) m/e 640 (M+H)$^+$. Anal. Calc'd. for C$_{40}$H$_{37}$N$_3$O$_5$: C, 75.10; H, 5.83; N, 6.57. Found: C, 74.86; H, 6.11; N, 6.27.

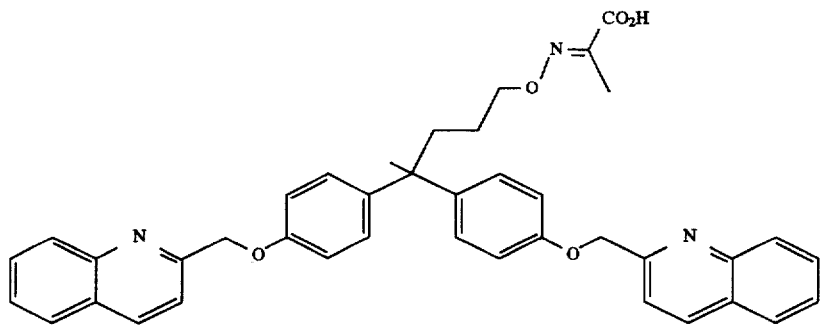

EXAMPLE 7

Preparation of |4,4-bis(4-(2-quinolylmethoxy)phenyl)pent-1-yl|oximinoacetic acid

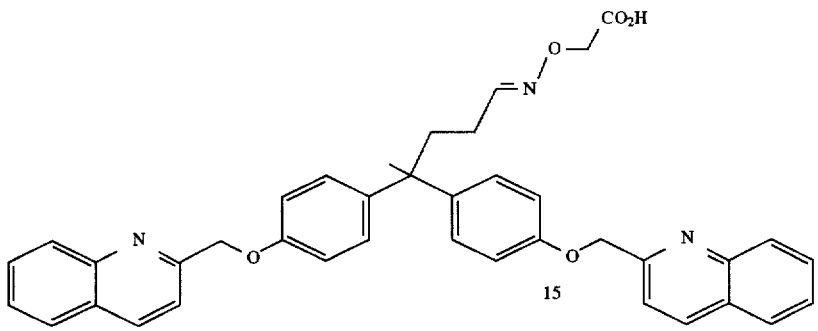

Step 1: 4,4-bis(4-(2-quinolylmethoxy)phenyl)pentanal

To a solution in DMSO (20 mL) of 4,4-bis(4-(2-quinolylmethoxy)phenyl)-pentan-1-ol (410 mg, 0.74 mmol), prepared as in Example 4, and 1,3-dicyclohexylcarbodiimnide (515 mg, 2.5 mmol) was added aqueous IM phosophoric acid (0.5 mL) and the resulting mixture was stirred at room temperature for 4 hours. Ethyl acetate (80 mL) was added and dicyclohexylurea was filtered off. The filtrate was washed with water and brine dried over $MgSO_4$, filtered, and concentrated in vacuo. The residue was purified by chromatography on silica gel (methylene chloride-ethyl acetate 9:1) to afford 280 mg of 4,4-bis(4-(2-quinolylmethoxy)phenyl)pentanal.

Step 2: [4,4-bis(4-(2-quinolylmethoxy)phenyl)pent-1yl] oximinoacetic acid

A mixture in dioxane (10 mL), methanol (10 mL) and water (5 mL) of the 4,4-bis(4-(2-quinolylmethoxy)phenyl) pentanal (280 mg, 0.5 mmol) prepared in step 1, carboxymethoxylamine hemihydrochloride (110 mg, 0.5 mmol), and sodium acetate trihydrate (69 mg, 0.5 mmol) was stirred at ambient temperature for 12 hours. The mixture was diluted with water and extracted with ethyl acetate. The ethyl acetate extract was washed with water and brine, dried over $MgSO_4$, filtered, and concentrated in vacuo. The residue was recrystallized from methylene chloride-hexane to afford 250 mg (80 %) of [4,4-bis(4-(2-quinolylmethoxy)phenyl)pent-1-yl]oximinoacetic acid: mp 78°–80° C.; $^1$NMR (300 MHz, DMSO—$d_6$) d 1.53 (s, 3H), 1.88 (m 1H), 2.05 (m, 1H), 2.22 (m, 2H), 4.40 and 4.45 (two s, 1:1, 2H), 5.34 (s, 4H), 6.75 and 7.45 (two t, 1:1,1H), 6.96 (d, 4H, J=9 Hz), 7.10 (dd, 4H, J=9.7 Hz), 7.64 (m, 4H), 7.78 (m, 2H), 8.00 (m, 4H), 8.41 (d, 2H, J=8 Hz), 12.62 (bs ,1H); MS (DCI—$NH_3$) m/e 626 (M+H)$^+$. Anal. Calc'd. for $C_{39}H_{35}N_3O_5 \cdot 0.5 H_2O$: C, 73.79; H, 5.72; N, 6.62. Found: C, 73.94; H, 6.13; N, 6.68.

EXAMPLE 8

Preparation of 4,4-bis(4-(2-benzothiazoylmethoxy)phenyl)pentanoic acid

The desired product was prepared according to the procedure of Example 1, except substituting 2-chloromethylbenzothiazole for 2-chloromethylquinoline: mp 185°–186° C.; $^1$H NMR (300 mHz, DMSO—$d_6$) d 1.60 (s, 3H), 1.94 (m, 2H), 2.29 (m, 2H), 5.05 (s, 4H), 7.01 (d, 4H, J=9 Hz), 7.13 (d, 4H, J=9 Hz), 7.50 (m, 4H), 8.03 (d, 2H, J=9 Hz), 8.13 (m, 2H), 12.04 (bs, 1 H); MS (DCI—$NH_3$) m/e 598 (M+$NH_4$)$^+$, 581 (M+H)$^+$. Anal. Calc'd. for $C_{33}H_{28}N_2O_4S_2$: C, 68.27; H, 4.86; N, 4.83. Found C, 68.06; H, 4.70; N, 4.64.

EXAMPLE 9

Preparation of 4,4-bis(4-(2-benzothiazoylmethoxy)phenyl)pentanoic acid sodium salt The desired salt was prepared according to the procedure of Example 2, except substituting 4,4-bis(4-(2-benzothiazoylmethoxy)phenyl)pentanoic acid, prepared as in Example 8, for 4,4-bis(4-(2-quinolylmethoxy)phenyl) pentanoic acid: mp 105°–108° C.; $^1$H NMR (300 mHz, DMSO—$d_6$) d 1.48 (s, 3H), 1.58 (m, 2H), 2.19 (m, 2H), 5.54 (s, 4H), 6.98 (d, 4H, J=9 Hz), 7.10 (d, 4H, J=9 Hz), 7.5 (m, 4H), 8.01 (d, 2H, J=9 Hz), 8.11 (d, 2H, J=9 Hz). MS (FAB) m/e 625 (M+Na)$^+$, 603 (M+H)$^+$. Anal. Calc'd. for $C_{33}H_{27}N_2O_4SNa \cdot 1.5 H_2O$: C, 62.95; H, 4.80; N, 4.45. Found: C, 63.11; H, 4.72; N, 4.26.

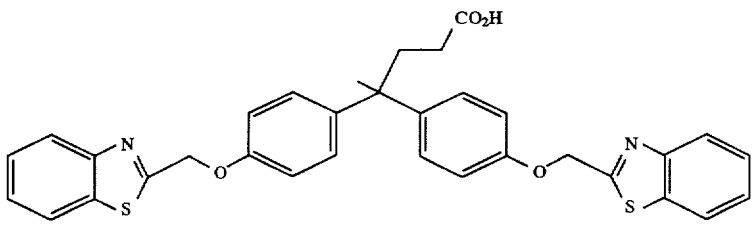

EXAMPLE 10

Preparation of 4,4-bis(4-(7-chloro-2-quinolylmethoxy)phenyl)pentanoic acid

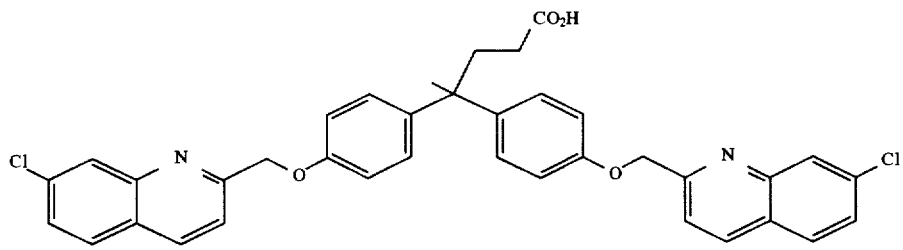

The desired compound was prepared according to the procedure of Example 1, except substituting 2 chloromethyl-7-chloroquinoline for 2-chloromethylquinoline: mp 88°–90° C.; $^1$H NMR (300 mHz, DMSO—$d_6$) d 1.51 (s, 3H), 1.95 (m, 2H), 2.28 (m, 2H), 5.33 (s, 4H), 6.97 (d, 4H, J=9 Hz), 7.09 (d, 4H, J=9 Hz), 7.66 (dd, 2H, J=9, 2 Hz), 7.71 (d, 2H, J=9 Hz), 8.06 (m, 4H), 8.47 (d, 2H, J=9 Hz), 12.03 (bs,1H); MS (DCI—$NH_3$) m/e 637 (M+H)$^+$. Anal. Calc'd. for $C_{37}H_{30}Cl_2N_2O_4$: C, 69.81; H, 4.75; N, 4.40. Found: C, 69.77; H, 5.05; N, 4.17.

EXAMPLE 11

Preparation of 4,4-bis(4-(6-fluoro-2-quinolylmethoxy)phenyl)pentanoic acid sodium salt

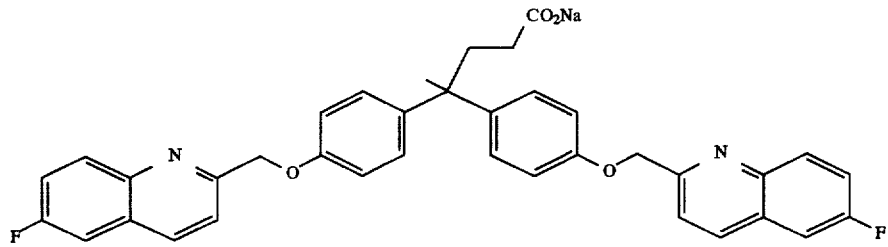

Step 1: 4,4-bis(4-(6-fluoro-2-quinolylmethoxy)phenyl) pentanoic acid

The desired compound was prepared according to the procedure of Example 1, except substituting 2 chloromethyl-6-fluoroquinoline for 2-chloromethylquinoline.

Step 2: 4,4-bis(4-(6-fluoro-2-quinolylmethoxy)phenyl) pentanoic acid sodium salt The desired salt was prepared according to the procedure of Example 2, except substituting 4,4-bis(4-(6-fluoro-2-quinolylmethoxy)phenyl)pentanoic acid, prepared as in step 1, for 4,4-bis(4-(2-quinolylmethoxy)phenyl)pentanoic acid: mp 97°–99° C.; $^1$H NMR (300 mHz, DMSO—$d_6$) d 1.48 (s, 3H), 1.70 (m, 2H), 2.1 (m, 2H), 5.31 (S, 4H), 6.95 (d, 4H, J=9 Hz), 7.08 (d, 4H, J=9 Hz), 7.68 (m, 4H), 7.80 (dd, 2H, J=9, 3 Hz), 8.08 (dd, 2H, J=9, 6 Hz), 8.41 (d, 2H); MS (FAB) m/e 627 (M+Na)$^+$, 605 (M+H)$^+$. Anal. Calc'd. for: $C_{37}H_{29}F_2N_2O_4Na$: C, 70.92; H, 4.76; N 4.47. Found: C, 70.79; H, 4.84; N, 4.30.

EXAMPLE 12

Preparation of 2.2-bis(4-(2-quinolylmethoxy) phenyl)propionic acid

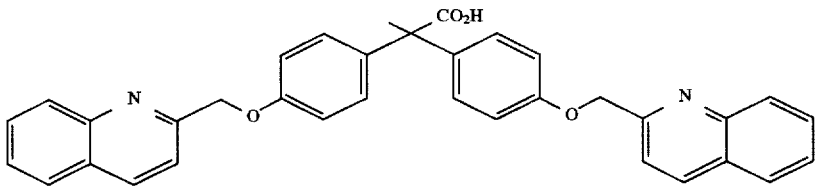

Step 1: 2.2-bis(4-hydroxyphenyl)propionic acid

To a cooled mixture of phenol (9.4 g, 0.1 mol), pyruvic acid (4.4 g, 0.05 mol), and water was added concentrated $H_2SO_4$ (4.5 mL, 18.0 g) dropwise with stirring. After 15 minutes the ice bath was removed and the reaction was warmed to room temperature and stirred for 18 hours. The reaction mixture was diluted with ethyl ether/water (200 ml 1:1) and the layers were separated. The organic layer was extracted with saturated aqueous $NaHCO_3$. The aqueous extract was then acidified, extracted with ethyl ether, dried over $MgSO_4$, filtered, and concentrated in vacuo to give 2.2-bis(4-hydroxyphenyl)propionic acid (6.2 g) as a colorless sticky oil.

Step 2: 212-bis(4-(2-quinolylmethoxy)phenyl)propionic acid

The desired compound was prepared according to the method of Example 1, except substituting 2,2-bis(4-hydroxyphenyl)propionic acid, prepared as in step 1, for 4,4-bis(4-hydroxyphenyl)pentanoic acid: mp 208°–210° C.; $^1H$ NMR (300 mHz, DMSO—$d_6$) d 1.75 (s, 3H), 5.33 (s, 4H), 7.01 (d, 4H, J=9 Hz), 7.12 (d, 4H, J=9 Hz), 7.63 (m, 4H), 7.78 (m, 2H), 8.01 (t, 4H, J=8 Hz), 8.42 (d, 2H, J=8 Hz), 12.65 (bs, 1 H); MS (DCI—$NH_3$) m/e 541 (M+H)$^+$. Anal. Calc'd. for $C_{35}H_{28}N_2O_4 \cdot H_2O$: C, 75.19; H, 5.28; N, 5.02. Found: C, 74.85; H, 4.89; N, 4.92.

EXAMPLE 13

Preparation of 3.3-bis(4-(2-quinolylmethoxy) phenyl)butanoic acid

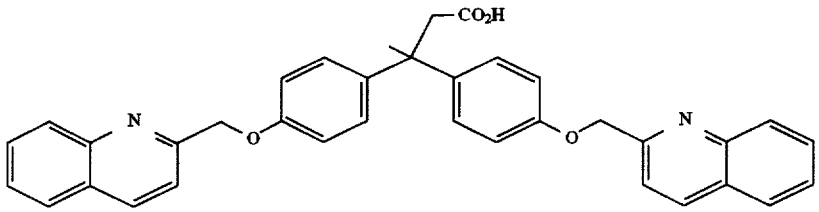

The desired product was prepared according to the procedure of Example 12, except substituting ethyl acetoacetate for pyruvic acid and hydrolysis of the intermediate ethyl ester as described in Example 1, step 3: mp 94°–96° C.; $^1H$ NMR (300 mHz, DMSO—$d_6$) d 1.75 (s, 3H), 3.02 (s, 2H), 5.32 (s, 4H), 6.95 (d, 4H, J=9 Hz), 7.11 (d, 4H, J=9 Hz), 7.65 (m, 4H), 7.78 (m, 2H), 8.01 (t, 4H, J=8 Hz), 8.41 (d, 2H, J=8 Hz), 11.83 (bs, 1H); MS (DCI—$NH_3$) m/e 555 (M+H)$^+$. Anal. Calc'd. for $C_{36}H_{30}N_2O_4 \cdot 0.5H_2O$: C, 76.71; H, 5.54; N, 4.95. Found: C, 76.23; H, 5.43; N, 4.66.

EXAMPLE 14

Preparation of 5,5-bis(4-(2-quinolylmethoxy)phenyl)hexanoic acid

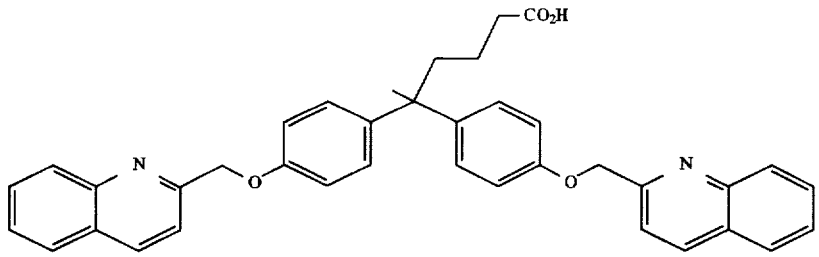

The desired compound was prepared according to the procedure of Example 12, except substituting 4-acetyl butyric acid for pyruvic acid: mp 87°–89° C.; $^1$H NMR (300 mHz, DMSO—$d_6$) d 1.25 (m, 2H), 1.51 (s, 3H), 2.0 (m, 2H), 2.17 (t, 2H, J=8 Hz), 5.32 (s, 4H), 6.96 (d, 4H, J=9 Hz), 7.09 (d, 4H, J=9 Hz), 7.62 (m, 7.68 (d, 2H, J=9 Hz), 7.78 (m, 2H), 8.02 (t, 2H, J=8 Hz), 8.41 (d, 2H, J=8 Hz), 11.97 (bs, 1H); MS (FAB) n/e 583 (M+H)$^+$. Anal. Calc'd. for $C_{38}H_{34}N_2O_4$: C, 78.34; H, 5.87; N, 4.81. Found: C, 77.97; H, 6.0; N, 4.63.

EXAMPLE 15

Preparation of 5,5-bis(4-(2-quinolylmethoxy)phenyl)hexanoic acid sodium salt

The desired compound was prepared according to the method of Example 2, except substituting 5,5-bis(4-(2-quinolylmethoxy)phenyl)hexanoic acid, prepared as in Example 14, for 4,4-bis(4-(2-quinolylmethoxy)phenyl)pentanoic acid: $^1$H NMR (300 mHz, DMSO—$d_6$) d 1.20 (m, 2H), 1.51 (s, 3H), 1.81 (t, 2H, J=8 Hz), 1.95 (m, 2H), 5.32 (s, 4H), 6.94 (d, 4H, J=9 Hz), 7.09 (d, 4H, J=9 Hz), 7.61 (t,2H, J=8 Hz), 7.68 (d, 2H, J=8 Hz), 7.80 (m, 2H), 8.01 (t, 4H, J=8 Hz), 8.42 (d, 2H, J=8 Hz). MS (FAB) m/e 605 (M+Na)$^+$, 583 (M+H)$^+$. Anal. Calc'd. for $C_{38}H_{33}N_2O_4Na.0.5 H_2O$: C, 74.39; H, 5.55; N, 4.57. Found: C, 74.64; H, 5.64; N, 4.36.

EXAMPLE 16

Preparation of 4,4-bis-(4-(2-pyridylmethoxy)phenyl)pentanoic acid sodium salt

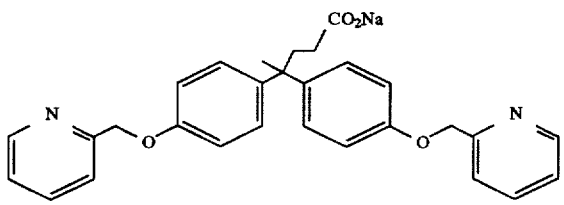

Step 1: 4,4-bis-(4-(2-pyridylmethoxy)phenyl)pentanoic acid

The desired compound was prepared according to the procedure of Example 1, except substituting 2-picolyl chloride for 2-chloromethylquinoline.

Step 2: 4,4-bis-(4-(2-pyridylmethoxy)phenyl)pentanoic acid sodium salt

The desired compound was prepared according to Example 2, except substituting 4,4-bis-(4-(2-pyridylmethoxy)phenyl)pentanoic acid, prepared as in step 1, for 4,4-bis(4-(2-quinolylmethoxy)phenyl)pentanoic acid: $^1$H NMR (300 mHz, DMSO—$d_6$) d 1.49 (s, 3H), 1.53 (m, 2H), 2.21 (m, 2H), 5.13 (s, 4H), 6.92 (d, 4H, J=9 Hz), 7.08 (d, 4H, J=9 Hz), 7.34 (m, 2H), 7.51 (d, 2H, J=9 Hz), 7.34 (m, 2H), 7.51 (d, 2H, J=9 Hz), 7.84 (dt, 2H, J=9, 2 Hz), 8.56 (d, 2H, J=4.5 Hz); MS (FAB) nme 491 (M+Na)$^+$, 469 (M+H)$^+$. Anal. Calc'd. for $C_{29}H_{27}N_2O_4Na.0.5H_2O$: C, 69.72; H, 5.57; N, 5.57. Found: C, 69.45; H, 5.59; N, 5.29.

EXAMPLE 17

Preparation of 4,4-bis-(4-(2-quinoxylmethoxy)phenyl)pentanoic acid sodium salt

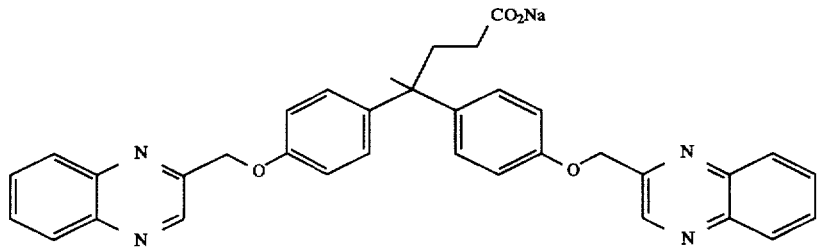

The desired compound was prepared according to Example 16, except substituting 2-chloromethylquinoxaline for 2-picolyl chloride: $^1$H NMR (300 mHz, DMSO—$d_6$) d 1.49 (s, 3H), 1.66 (m, 2H), 2.22 (m, 2H), 5.42 (s, 4H), 6.99 (d, 4H, J=9 Hz), 7.11 (d, 4H, J=9 Hz), 7.88 (m, 4H), 8.11 (m, 4H), 9.11 (s, 2H); MS (FAB) m/e 593 (M+Na)$^+$, 571 (M+H)$^+$. Anal. Calc'd. for $C_{35}H_{29}N_4O_4Na \cdot H_2O$: C, 68.91; H, 5.11; N, 9.19. Found: C, 68.58, H, 5.15, N, 8.99.

EXAMPLE 18

Preparation of 4,4-bis(4-(1-methyl-2-benzimidazolylmethoxy)phenyl)pentanoic acid

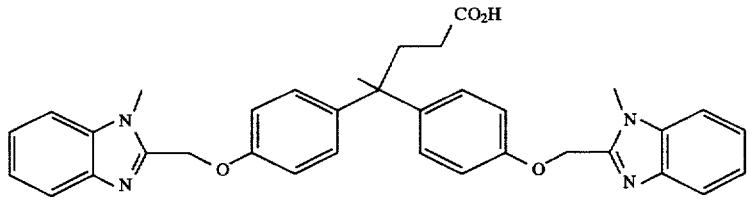

The desired product was prepared according to the procedure of Example 1, except substituting 1-methyl-2-chloromethylbenzimidazole for 2-chloromethyl-quinoline: mp 110°–112° C.; $^1$H NMR (300 MHz; DMSO—$d_6$) d 1.52 (s, 3H), 1.95 (m, 2H), 2.28 (m, 2H), 3.85 (s, 6H), 5.37 (s, 4H), 7.02 (d, 4H, J=9 Hz), 7.10 (d, 4H, J=9 Hz), 7.35 (m, 4H), 7.56 (m, 2H), 7.64 (m, 2H), 12.00 (bs, 1 H); MS (FAB+) m/e 575 (M+H)$^+$; (FAB–) m/e 573 (M–H)$^-$. Anal. Calc'd. for $C_{35}H_{34}N_4O_4 \cdot H_2O$: C, 70.93; H, 6.12; N, 9.45. Found: C, 70.79; H, 6.11; N, 8.87.

EXAMPLE 19

Preparation of 4,4-bis(4-(1-methyl-2-benzimidazolylmethoxy)phenyl)pentanoic acid sodium salt The desired product was prepared according to the method of Example 2, except substituting 4,4-bis(4-(1-methyl-2-benzimidazolylmethoxy)phenyl)pentanoic acid, prepared as in Example 18, for 4,4-bis(4-(2-quinolylmethoxy)phenyl)pentanoic acid: $^1$H NMR (300 MHz, DMSO—$d_6$) d 1.48 (s, 3H), 1.60 (m, 2H), 2.20 (m, 2H), 3.85 (s, 6H), 5.35 (s, 4H), 7.00 (d, 4H, J=9 Hz), 7.09 (d, 4H, J=9 Hz), 7.35 (m, 4H), 7.56 (m, 2H), 7.64 (m, 2H); MS (FAB+) m/e 597 (M+Na)$^+$, 575 (M+H)$^+$, (FAB–) m/e 573 (M–H)$^-$. Anal. Calc'd. for $C_{35}H_{33}N_4O_4Na \cdot 1.5H_2O$: C, 67.53; H, 5.81; N, 9.00. Found: C, 67.50; H, 5.85; N, 8.56.

EXAMPLE 20

Preparation of 4,4-bis(3-chloro-4-(2-quinolylmethoxy)phenyl)pentanoic acid

Step 1: 4,4-bis(3-chloro-4-(2-quinolylmethoxy)phenyl) pentanoic acid methyl ester A mixture of 4,4-bis(4-hydroxyphenyl)pentanoic acid (5.72 g, 20 mmol), and N-chlorosuccinimide (5.84 g, 44 mmol) in chloroform (120 mL) and dioxane (30 mL) was heated at reflux for 5 hours. The reaction mixture was concentrated in vacuo and the residue was dissolved in methanol (100 mL). The methanol solution was cooled to –70° C., thionyl chloride (3 mL) was added, and the mixture was left at ambient temperature for 16 hours. The methanol was removed in vacuo and DMF (150 mL), potassium carbonate (13.8 g, 100 mmol) and 2-chloromethyl-quinoline hydrochloride (9 g, 42 mmol) were added to the residue. The resulting mixture was stirred at room temperature for 10 hours. The mixture was diluted with water (400 mL) and extracted with ethyl acetate. The organic layer was washed with water and brine, dried over $MgSO_4$, filtered, and concentrated in vacuo. The residue was purified by chromatography on silica gel (methylene chloride-ethyl acetate 15:1) to afford 8 g of 4,4-bis(3-chloro-4-(2-quinolylmethoxy)phenyl)pentanoic acid methyl ester and 1.2 g of 4-(3-chloro-4(2-quinolylmethoxy)phenyl)-4-(3,5-dichloro-4-(2-quinolylmethoxy) phenyl)pentanoic acid methyl ester.

Step 2: 4,4-bis(3-chloro-4-(2-quinolylmethoxy)phenyl) pentanoic acid The desired compound was prepared according to the method of Example 1, step 3, except substituting 4,4-bis(3-chloro-4-(2-quinolylmethoxy)phenyl)pentanoic acid methyl ester, prepared as in step 1, for 4,4-bis(4-(2-quinolylmethoxy)phenyl)-pentanoic acid methyl ester: mp 91°–94° C.; $^1$H NMR (300 MHz, DMSO—$d_6$) d 1.53 (s, 3H), 1.96 (m, 2H), 2.30 (m, 2H), 5.44 (s, 4H), 7.09 (dd, 2H, J=3, 9 Hz), 7.20 (d, 2H, J=9 Hz), 7.24 (d, 2H, J=3Hz), 7.62 (m, 2H), 7.71 (d, 2H, J=9 Hz), 7.80 (m, 2H), 8.00 (m, 4H), 8.44 (d, 2H, J=9 Hz), 12.08 (bs, 1H); MS (DCI-NH$_3$) m/e 637 (M+H)$^+$. Anal. Calc'd. for $C_{37}H_{30}Cl_2N_2O_4 \times H_2O$: C, 67.79; H, 4.92; N, 4.27. Found: C, 68.02; H, 4.85; N, 3.94.

EXAMPLE 21

Preparation of 4,4-bis(3-chloro-4-(2-quinolylmethoxy)phenyl)pentanoic acid sodium salt The desired product was prepared according to the method of Example 2, except substituting 4,4bis(3-chloro-

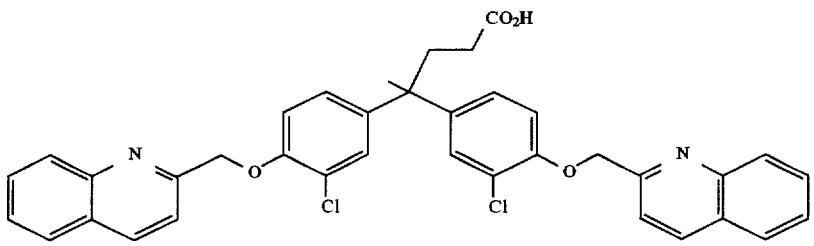

4-(2-quinolylmethoxy)phenyl)pentanoic acid, prepared as in Example 20, for 4,4-bis(4-(2-quinolylmethoxy)phenyl) pentanoic acid: $^1$H NMR (300 MHz, DMSO—$d_6$) d 1.47 (s, 3H), 1.85 (m, 2H), 2.25 (m, 2H), 5.43 (s, 4H), 7.06 (dd, 2H, J=3, J=9 Hz), 7.18 (d, 2H, J=9 Hz), 7.22 (d, 2H, J=3Hz), 7.61 (m, 2H), 7.71 (d, 2H, J=9 Hz), 7.79 (m, 2H), 8.00 (m, 4H), 8.42 (d, 2H, J=9 Hz); MS (FAB+) m/e 659 (M+Na)$^+$, 637 (M+H)$^+$, MS (FAB−) m/e 635 (M−H)$^−$. Anal. Calcd. for $C_{37}H_{29}Cl_2N_2O_4Na$: C, 67.38; H, 4.43; N, 4.25. Found: C, 67.74; H, 4.89; N, 3.96.

EXAMPLE 22

Preparation of |4,4-bis(3-chloro-4-(2-quinolylmethoxy)-phenyl)pent-1-yl|-2-iminoxypropionic acid sodium salt

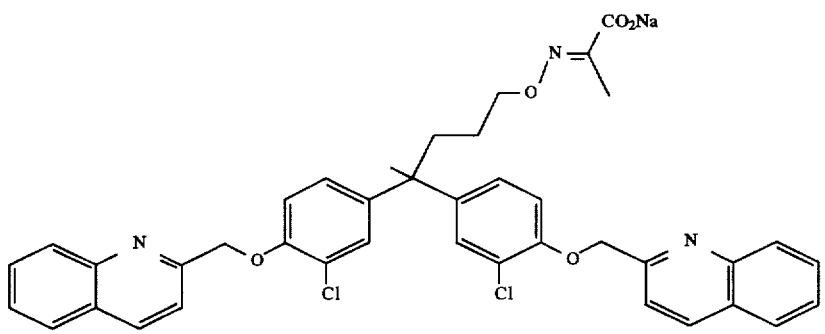

Step 1: 4,4-bis(3-chloro-4-(2-quinolylmethoxy)phenyl) pentan-11-ol

The desired compound was prepared according to the method of Example 4, except substituting 4,4-Bis(3-chloro-4-hydroxyphenyl)pentanoic acid, prepared as in Example 20, for 4,4-bis(4-(2-quinolylmethoxy)phenyl)pentanoic acid.

Step 2: O-[4,4-bis(3-chloro-4-(2-quinolylmethoxy)phenyl) pent-1yl]hydroxylamine

The desired compound was prepared according to the method of Example 5, steps 1 and 2, except substituting 4,4-bis(3-chloro-4-(2-quinolylmethoxy)phenyl)-pentan-1-ol, prepared as in step 1, for 4,4-bis(4-(2-quinolylmethoxy) phenyl)pentan-1-ol.

Step 3: [4,4-bis(3-chloro-4-(2-quinolylmethoxy)-0phenyl) pent-1-yl]-2-iminoxypropionic acid The desired compound was prepared according to the method of Example 6, except substituting O-[4,4-bis(3-chloro-4-(2-quinolylmethoxy)phenyl)pent-1 -yl] hydroxylamine, prepared as in step 2, for O-[4,4-bis(4-(2-quinolylmethoxy)-phenyl)pent-1-yl]hydroxylamine. Step 4: [4,4-bis(3-chloro-4-(2-quinolylmethoxy)-phenyl)pent-1-yl] -2-iminoxyprogionic acid sodium salt The desired compound was prepared according to the method of Example 2, except substituting |4,4-bis(3-chloro-4-(2-quinolylmethoxy)phenyl)pent-1-yl|-2-imidnoxypropionic acid, prepared as in step 3, for 4,4-bis (4-(2-quinolylmethoxy)phenyl)pentanoic acid: $^1$H NMR (300 MHz, DMSO—$d_6$) d 1.31 (m, 2H), 1.54 (s, 3H), 1.79 (s, 3H), 2.04 (m, 2H), 3.93 (t, 2H, J=7 Hz), 5.42 4H), 7.09 (dd, 2H, J=3, 9 Hz), 7.20 (m, 4H), 7.62 (m, 2H), 7.71 (d, 2H, J=8 Hz), 7.80 (m, 2H), 8.00 (m, 4H), 8.44 (d, 2H, J=8 Hz); MS (FAB+) m/e 730 (M+Na)$^+$, 708 (M+H)$^+$, (FAB−) m/e 706 (M−H)$^−$. Anal. Calc'd. for $C_{40}H_{34}N_3Cl_2O_5Na·H_2O$: C, 64.17; H, 4.84; N, 5.61. Found: C, 64.40; H, 4.87; N, 5.37.

EXAMPLE 23

Preparation of 4,4-bis(4-(2-quinolylmethoxy)-o0 phenyl)pentanoic acid N,N-diethylhydroxylamine ester

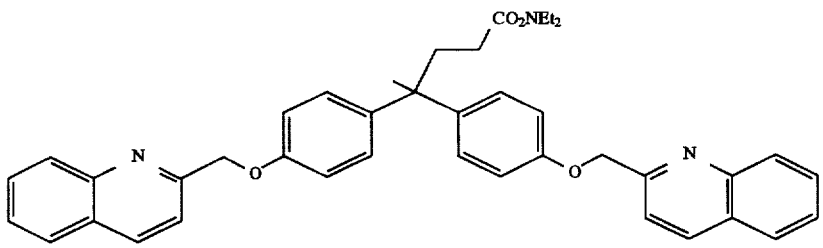

To a solution in methylene chloride (10 mL) of 4,4-bis-(4-(2-quinolyl-methoxy)phenyl) pentanoic acid (570 mg, 1 mmol), prepared as in Example 1, was added 1,1'-carbonyldiimidazole (162 mg, 1.1 mmol) and the resulting mixture was stirred at room temperature for 25 minutes. N,N-Diethylhydroxylamine (0.14 mL, 1.2 mmol) was then added and stirring was continued for additional 30 minutes. The solution was concentrated in vacuo and the residue was purified by chromatography on silica gel (methylene chloride-ethyl acetate 4:1) to afford 420 mg (66%) of 4,4-bis(4-(2-quinolylmethoxy)phenyl)pentanoic acid N,N-diethylhydroxylamine ester: $^1$H NMR (300 MHz, DMSO—$d_6$) d 0.92 (t, 6H, J=7 Hz), 1.51 (s, 3H), 2.03 (m, 2H), 2.30 (m, 2H), 2.75 (q, 4H, J=7 Hz), 5.32 (s, 4H), 6.98 (d, 4H, J=9 Hz), 7.09 (d, 4H, J=9 Hz), 7.65 (m, 4H), 7.78 (m, 2H), 8.00 (m, 4H), 8.41 (d, 2H, J=9 Hz); MS (DCI—NH$_3$) m/e 640

(M+H)+. Anal. Calc'd. for C41H41N3O4: C, 76.97; H, 6.46; N, 6.57. Found: C, 76.82; H, 6.49; N, 6.50.

EXAMPLE 24

Preparation of 2,2-bis(4-(2-quinolylmethoxy) phenyl)butyric acid

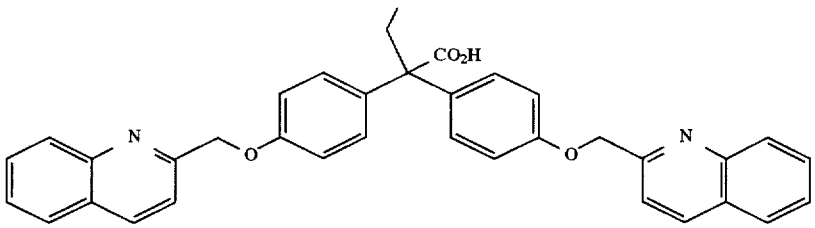

The desired product was prepared according to the procedure of Example 12, except substituting 2-ketobutyric acid for pyruvic acid: mp 83°–92° C.; $^1$H NMR (300 MHz, DMSO—d$_6$) d 0.65 (m, 3H), 2.25 (m, 2H), 5.35 (s, 4H), 7.00 (d, 4H, J 9 Hz), 7.16 (d, 4H, J=9 Hz), 7.63 (m, 2H), 7.68 (d, 2H, J=9 Hz), 7.79 (m, 2H), 8.01 (m, 4H), 8.42 (d, 2H, J=9 Hz), 12.54 (br s, 1H); MS (DCI—NH$_3$) m/e 555 (M+H)+. Anal. Calc'd. for C$_{36}$H$_{30}$N$_2$O$_4$·0.55 H$_2$O: C, 76.59; H, 5.55; N, 4.96. Found: C, 76.90; H, 5.78; N, 4.57.

EXAMPLE 25

Preparation of 1,1-bis(4-(2-quinolylmethoxy) phenyl)ethanol

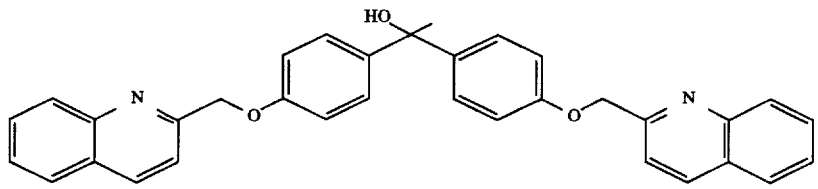

Step 1: bis(4-(2-quinolylmethoxy)phenyl) ketone

To a solution of 4-4'-dihydroxybenzophenone (4.22 g, 20 mmol) and K$_2$CO$_3$ (16.5 g, 120 mmol) in DMF (75 mnL) was added 2-chloromethylquinoline hydrochloride (8.56 g, 40 mmol) and the resulting solution was stirred at 60° C. or 16 hours. The reaction mixture was then poured into ice water (100 mL and the resulting solid was collected by filtration, slurried in 20% ether/hexane, filtered, and dried in vacuo to afford bis(4-(2-quinolylmethoxy)phenyl) ketone (9.3 g, 94%) as white solid.

Step 2: 1,1-bis(4-(2-quinolylmethoxy)phenyl)ethanol

To a −78° C. solution in THF (20 mL) of bis(4-(2-quinolylmethoxy)phenyl) ketone (992 mg, 2 mmol), prepared as in step 1, was added methylmagnesium bromide (3M solution in ethyl ether, 0.8 mL, 2.4 mmol) and the resulting mixture was stirred at room temperature for 12 hours. The mixture was then quenched with saturated aqueous ammonium chloride and extracted with ethyl acetate. The organic phase was washed with water and brine, dried over MgSO$_4$, filtered, and concentrated in vacuo. The residue was purified by chromatography on silica gel (methylene chloride-ethyl acetate 4:1) to afford 920 mg (90%) of 1,1-bis(4-(2-quinolylmethoxy)phenyl)ethanol mp 129°–131° C.; $^1$H NMR (300 MHz, DMSO—d$_6$) d 1.74 (s, 3H), 5.32 (s, 4H), 5.48 (s, 1H), 6.95 (d, 4H, J=9 Hz), 7.30 (d, 4H, J=9 Hz), 7.63 (m, 4H), 7.78 (m, 2H), 8.01 (m, 4H), 8.39 (d, 2H, J=8 Hz); MS (DCI—NH$_3$) m/e 513 (M+H)+. Anal Calc'd. for C$_{34}$H$_{28}$N$_2$O$_3$: C, 79.67; H, 5.51; N, 5.46. Found: C, 79.48; H, 5.62; N, 5.25.

EXAMPLE 26

Preparation of 2,2-dimethyl-3,3-bis(4-(2-quinolylmethoxy)phenyl)propionic acid sodium salt

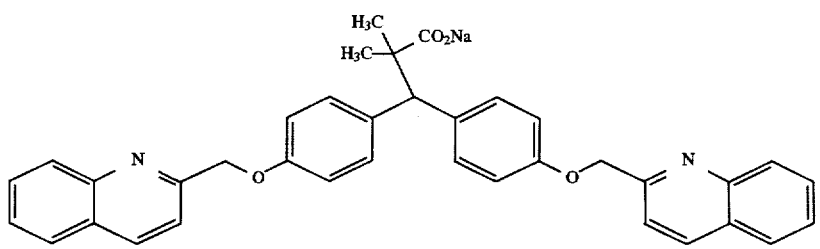

Step 1: 2,2-dimethyl-3,3-bis(4-hydroxyphenyl)propionic acid methyl ester

To a stirred 0° C. solution in methanol (2 mL) of phenol (3.76 g, 40 mmol) and methyl-3-carboxaldehyde-2,2-dimethyl propionate (2.6 g, 20 mmol) was added dropwise 10 g of sulfuric acid. The deep red solution was stirred in the ice bath for 0.5 hours and at room temperature for an additional 3 hours. The mixture was poured into 300 mL water and extracted with ether (2×300 mL). The combined ether extracts were washed twice with saturated aqueous NaHCO$_3$, twice with water, and once with brine. The organic layer was dried over MgSO$_4$, filtered, and concentrated in vacuo. The residue purified by column chromatography on silica gel (35% ethyl acetate/hexanes) to give 1.1 g (18%) of methyl ester intermediate as a white semisolid.
Step 2: 2,2-dimethyl-3,3-bis(4-(2-quinolylmethoxy)phenyl) propionic acid methyl ester To a stirred solution in DMF (50 mL) of 2,2-dimethyl-3,3-bis(4-hydroxy-phenyl)propionic acid methyl ester (1.1 g, 3.7 mmol), prepared as in step 1, was added Cs$_2$CO$_3$ (2.5 g, 7.7 mmol) and the mixture stirred 0.5 hours at room temperature. 2-Chloromethyquinoline (1.37g, 7.7 mmol) was added as a solid in small portions. The reaction mixture was stirred overnight at room temperature. The mixture was poured into 300 mnL of water and extracted with ether (2×200 mL). Brine was added to the aqueous layer and it was extracted twice with ether. The combined ether extracts were washed with brine, dried over MgSO$_4$, filtered, and concentrated in vacuo to give a light yellow oil. Chromatography on silica gel (40% ethyl acetate/hexanes) gave 1.68 g (78%) of 2,2-dimethyl-3,3-bis(4-(2-quinolyl-methoxy) phenyl)propionic acid methyl ester as a white foam.

Step 3: 2,2-dimethyl-3,3-bis(4-(2-guinolylynethoxy) phenyl)propionic acid

To a solution in methanol (8 mL) and THF (4 mL) of 2,2-dimethyl-3,3-bis(4-(2-quinolylmethoxy)phenyl) propionic acid methyl ester (0.4 g, 0.69 mmol), prepared as in step 2, was added LiOH.H$_2$O (4 ml, 4 mmole, 1M solution) dropwise, and the mixture was stirred overnight after which an additional 2 mL of the LiOH solution was added and the mixture was stirred an additional 24 hours. The mixture was concentrated to dryness, acidified with excess 0.5M citric acid, diluted with water and extracted with ethyl acetate (3×50 mL). The combined organic layers were washed with brine, dried over MgSO$_4$, filtered, and concentrated in vacuo. 1 o Purification by chromatography on silica gel (7% MeOH/CH$_2$Cl$_2$) provided 0.16 g (40%) of 2,2-dimethyl-3,3-bis(4-(2-quinolylmethoxy)phenyl) propionic acid as a white solid: mp 124°–127° C. Anal. Calc'd. for C$_{37}$H$_{32}$N$_2$O$_4$: C, 78.14; H, 5.67; N 4.92. Found C, 77.45; H, 5.74; N, 4.67.

Step 4: 2,2-dimethyl-3,3-bis(4-(2-quinolylmethoxy)phenyl) propionic acid sodium salt To a solution in THF (10 mL) and ethanol (8 mL) of 2,2-dimethyl-3,3-bis(4-(2-quinolylmethoxy)phenyl) proppionic acid (0.128 g, .225 mmol), prepared as in step 3, was added one equivalent of NaOH (2.3 mL, 0.1 N NaOH). The reaction was stirred for 1 hour at room temperature, concentrated, and dried under high vacuum to provide 2,2-dimethyl-3,3-bis(4-(2-quinolylmethoxy)phenyl) propionic acid sodium salt as a white powder 0.13 g (99%): mp 250°–255° C. (dec); $^1$H NMR (300 MHz, DMSO—d$_6$) d 0.91 (s, 6H), 4.46 (s, 1H), 5.29 (s, 4H), 6.87 (d, 4H, J=9 Hz), 7.15 (d, 4H, J=9 Hz), 7.61 (m, 2H), 7.67 (d, 4H, J=9 Hz), 7.78 (m, 2H), 8.00 (t, 4H, J=9 Hz), 8.40 (d, 2H, J=9 Hz); MS m/e (FAB+) 569 (M+H)$^+$, (FAB–) 567 (M–H)$^−$. Anal. Calc'd. for C$_{37}$H$_{31}$N$_2$O$_4$Na.0.5 H$_2$O: C, 74.10; H, 5.37; N 4.67. Found C, 74.02; H, 5.24; N, 4.50.

EXAMPLE 27

Preparation of [2,2-dimethyl-3,3-bis(4-(2-quinolylmethoxy)phenyl)prop-1-yl]oximinoacetic acid sodium salt

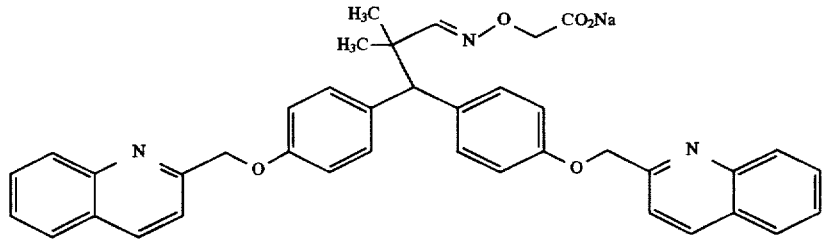

Step 1: 2,2-dimethyl-3,3-bis(4-(2-guinolylmethoxy)phenyl) propan-1-ol

To a stirred solution in THF (50 mL) at ambient temperature of 2,2-dimethyl-3,3-bis(4-(2-quinolylmethoxy)phenyl) propionic acid methyl ester (1.33 g, 2.28 mmole), prepared as in Example 26, step 2, was added LiAlH$_4$ (0.09 g, 2.5 mmol) in a single portion. The mixture was stirred 3 hours at ambient temperature. Water (0.1 mL) was added followed by aqueous 1N NaOH (0.1 ml) and water (0.5 mL). The mixture was then concentrated to dryness and partitioned between water and ethyl acetate. The organic layer was washed with brine, dried over MgSO$_4$, filtered, and concentrated in vacuo. Purification by chromatography on silica gel (60% ethylacetate/hexanes) gave 1.01 g (80%) of 2,2-dimethyl-3,3-bis(4-(2-quinolylmethoxy)phenyl)-propan-1-ol as a yellow foam.

Step 2: 2,2-dimethyl-3,3-bis(4-(2-quinolylmethoxy)phenyl) propanal

To a −78° C. solution in methylene chloride (15 mL) of 2,2-dimethyl-3,3-bis(4-(2-quinolylmethoxy) phenyl) propan- -ol (0.4 g, 0.72 mmol), prepared as in step 1, and DMSO (0.17 g, 2.17 mmol) was added oxalyl chloride (0.14 g, 1.08 mmol) and the reaction mixture was stirred for 0.5 hours. Triethylamine (0.37 g, 3.6 mmol) was added via syringe, the ice bath was removed, and the reaction was allowed to warm to room temperature. The mixture was concentrated in vacuo and triturated with dry THF. The THF solution was filtered and washed with additional THF. The THF solution and washings were combined and concentrated in vacuo to give crude 2,2-dimethyl-3,3-bis(4-(2-quinolylmethoxy)phenyl)propanal which was used without further purification for oxime formation.

Step 3: [2,2-dimethyl-3,3-bis(4-(2-quinolylmethoxy) phenyl)prop-1-yl]oximinoacetic acid The desired compound was prepared according to the method of Example 7, step 2, except substituting 2,2-dimethyl-3,3-bis(4-(2-quinolylmethoxy)phenyl)-propanal, prepared as in step 2, for 4,4-bis(4-(2-quinolylmethoxy) phenyl)pentanal.

Step 4: [2,2-dimethyl-3,3-bis(4-(2-quinolylmethoxy)phenyl)prop-1-yl]oximinoacetic acid sodium salt The desired compound was prepared according to the method of Example 2, except substituting [2,2-dimethyl-3,3-bis(4-(2-quinolylmethoxy)phenyl)prop-1-yl] oximinoacetic acid, prepared as in step 2, for 4,4-bis(4-(2-quinolylmethoxy)-phenyl)pentanoic acid: $^1$H NMR (300 MHz, DMSO—$d_6$) d 1.03 (s, 6H), 3.89 (s, 1H), 4.06 (s, 2H), 5.32 (s, 4H), 6.97 (d, 4H, J=9 Hz), 7.31 (d, 4H, J=9 Hz), 7.46 (s, 1H), 7.65 (m, 4H), 7.78 (m, 2H), 8.01 (t, 4H, J=9 Hz), 8.40 (d, 2H, J=9 Hz); MS (FAB+) m/e 648 (M+Na)$^+$, 626 (M+H)$^+$.

EXAMPLE 28

Preparation of 2,2-dimethyl-3,3-bis(4-(2-quinolylmethoxy)phenyl)-1-propyliminoxyacetic acid

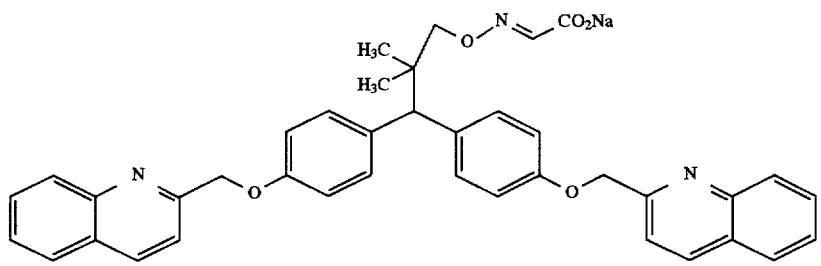

The desired compound was prepared according to the method of Example 5, except substituting 2,2-dimethyl-3,3-bis(4-(2-quinolylmethoxy)phenyl)propan-1-ol prepared as in Example 27, step 1, for 4,4-bis(4-(2-quinolylmethoxy) phenyl)pentan-1-ol: Amorphous white solid, softens at 125 °C. (decompose over next 40° C. range); $^1$H NMR (300 MHz, DMSO—$d_6$) d 0.94 (s, 6H), 3.68 (s, 2H), 3.90 (s, 1H), 5.41 (s, 4H), 6.96 (d, 4H, J=9 Hz), 7.36 (d, 4H, J=9 Hz), 7.41 (m, 2H), 7.63 (m, 4H), 7.78 (m, 2H), 8.00 (t, 4H, J=9 Hz), 8.39 (d, 2H, J=9 Hz). Anal. Calc'd. for $C_{39}H_{35}N_3O_5N.2.0$ $H_2O$:C , 70.78; H, 5.94; N 6.34. Found C, 71.25; H, 5.28; 6.39.

EXAMPLE 29

Preparation of 2,2-bis(4-(2-quinolymethoxy)phenyl) acetic acid

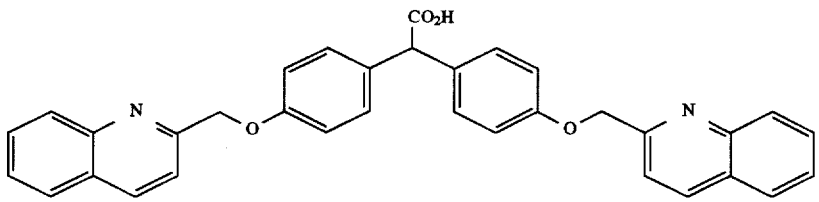

The title compound was prepared according to the procedure of Example 12, except substituting glyoxylic acid for pyruvic acid: mp 119°–128° C.; $^1$H NMR (300 MHz, DMSO—$d_6$) d 4.91 (s, 1H), 5.34 (s, 4H), 7.01 (d, 4H, J=7.5 Hz), 7.23 (d, 4H, J=7.5 Hz), 7.62 (t, 2H, J=7.5 Hz), 7.66 (d, 2H, J=7.5 Hz), 7.79 (t, 2H, J=7.5 Hz), 8.01 (t, 4H, J=7.5 Hz), 8.40 (d, 2H, J=7.5 Hz). MS (DCI—NH$_3$) m/e 527 (M+H)$^+$. Anal. Calc'd. for $C_{34}H_{26}N_2O_4 \cdot H_2O$: C, 74.98; H, 5.18;N, 5.14. Found: C, 74.97; H, 4.75; N, 5.02.

EXAMPLE 30

Preparation of 2,2-bis(4-(6-fluoro-2-quinolymethoxy)phenyl)acetic acid

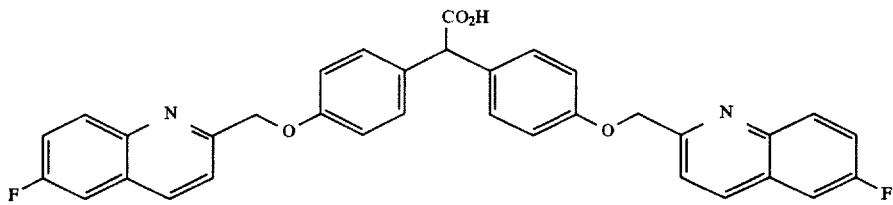

The title compound was prepared according to the procedure of Example 12, except substituting glyoxylic acid for pyruvic acid, and substituting 2-chloromethyl-6-fluoroquinoline for 2-chloromethylquinoline: mp 221°–223° C.; $^1$H NMR (300 MHz, DMSO—$d_6$) d 4.92 (s, 1H), 5.33 (s, 4H), 7.01 (d, 4H, J=7.5 Hz), 7.23 (d, 4H, J=7.5 Hz), 7.70 (m, 4H), 7.82 (dd, 2H, J=2.5, 9.0 Hz), 8.08 (m, 2H), 8.40 (d, 2H, J =7.5 Hz); MS (DCI—NH$_3$) m/e 563(M+H)$^+$. Anal. Calc'd. for $C_{34}H_{26}N_2O_4$: C, 72.59; H, 4.30; N, 4.97. Found: C, 72.36; H, 4.22; N, 4.76.

EXAMPLE 31

Preparation of 2,2-bis(4-(2-quinolylmethoxy)phenyl)eth-1-yloximinoacetic acid

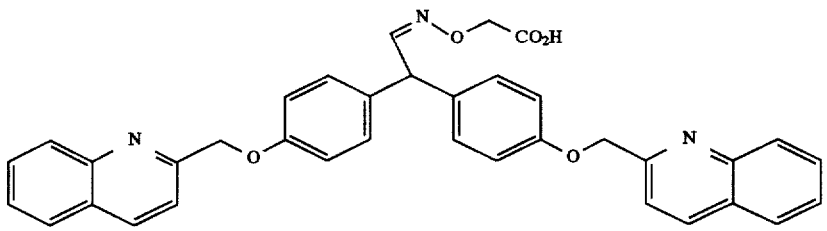

Step 1: 2,2-bis(4-(2-quinolymethoxy)phenyl)acetic acid methyl ester

The desired compound was prepared according to the method of Example 1, steps 1 and 2, except substituting 2,2-bis(4-hydroxyphenyl)acetic acid, prepared as in Example 29, for 4,4-bis(4-hydroxyphenyl)pentanoic acid.
Step 2: 2,2-bis(4-(2-quinolylmethoxy)phenyl)eth-1-yloximinoacetic acid The title compound was prepared according to the procedure of Example 27, steps 1-3, except substituting 2,2-bis(4-hydroxyphenyl)acetic acid methyl ester, prepared as in step 1, for methyl 2,2-dimethyl-3,3-bis(4-(2-quinolylmethoxy)phenyl)-propionate: mp 104°–108° C.; $^1$H NMR (300 MHz, DMSO—$d_6$) d 4.18 (s, 2H), 4.72 (d, 1H, J=7.5 Hz), 5.33 (s, 4H), 7.01 (d, 4H, J=7.5 Hz), 7.28 (d, 4H, J=7.5 Hz), 7.64 (m, 4H), 7.78 (t, 2H, J=7.5 Hz), 7.98 (m, 5H), 8.40 (d, 2H, J=7.5 Hz); MS (FAB+) m/e 584 (M+H)$^+$, (FAB-) m/e 582 (M—H)$^-$. Anal. Calc'd. for $C_{36}H_{29}N_3O_5$·1.5 H$_2$O: C, 70.80; H, 5.28; N, 6.88. Found: C, 71.07; H, 5.03; N, 6.61.

EXAMPLE 32

Preparation of 2,2-bis(4-(2-quinolylmethoxy)phenyl)eth-1-yloxinminoacetic acid sodium salt The desired compound was prepared according to the method of Example 2, except substituting 2,2-bis(4-(2-quinolylmethoxy)phenyl)-1-ethyloximinoacetic acid, prepared as in Example 3t1, for 4,4-bis(4-(2-quinolylmethoxy)phenyl)pentanoic acid: mp 138°–145° C.; $^1$H NMR (300 MHz, DMSO—$d_6$) d 4.04 (s, 2H), 4.12 (s, 1H), 4.72 (d, 1H, J=7.5 Hz), 5.33 (s, 4H), 7.01 (d, 4H, J=7.5 Hz), 7.28 (d, 4H, J 7.5 Hz), 7.64 (m, 4H), 7.78 (t, 2H, J=7.5 Hz), 8.00 (m, 4H), 8.40 (d, 2H, J=7.5 Hz). MS (DCI—NH$_3$) m/e 606 (M+Na)$^+$, 584 (M+H)$^+$.

EXAMPLE 33

Preparation of 3,3-bis(4-(2-quinolylmethoxy)phenyl)propionic acid

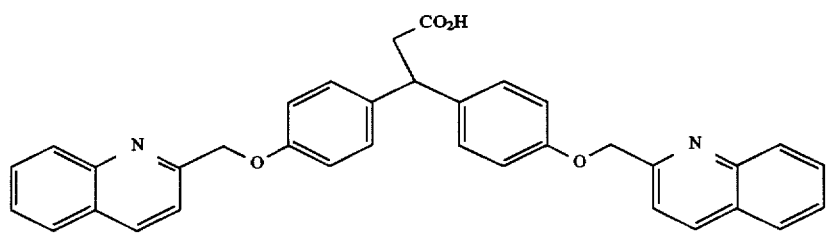

The desired compound was prepared according to the procedure of Example 26, except substituting ethyl 3,3-diethoxypropionate in ethanol for methyl 3-carboxaldehyde-2,2-dimethyl propionate in methanol: mp 94°–111° C.; ¹H NMR (300 MHz, DMSO—d₆) d 2.93 (d, 2H, J=7.5 Hz), 4.31 (t, 1H, J=7.5 Hz), 5.31 (s, 4H), 6.95 (d, 4H, J=8.0 Hz), 7.23 (d, 4H, J=8.0 Hz), 7.62 (m, 4H), 7.78 (t, 2H, J=7.5 Hz), 8.00 (t, 4H, J=7.5 Hz), 8.40 (d, 2H, J=7.5 Hz); MS (DCI—NH₃) $_{m/e}$ 541 (M+H)⁺. Anal. Calc'd. for $C_{35}H_{28}N_2O_4 \cdot H_2O$: C, 75.25; H, 5.41; N, 5.01. Found: C, 75.09; H, 5.19; N, 4.93.

EXAMPLE 34

Preparation of 3,3-bis(4-(2-quinolylmethoxy)phenyl)propionic acid sodium salt

The desired compound was prepared according to the method of Example 2, except substituting 3,3-bis(4-(2-quinolylmethoxy)phenyl)propionic acid, prepared as in Example 33, for 4,4-bis(4-(2-quinolylmethoxy)phenyl)pentanoic acid: mp 224°–232° C.; ¹H NMR (300 MHz, DMSO—d₆) d 2.44 (d, 2H, J=7.5 Hz), 4.31 (t, 1H, J=7.5 Hz), 5.29 (s, 4H), 6.89 (d, 4H, J=9.0 Hz), 7.12 (d, 4H, J=9.0 Hz), 7.62 (m, 4H), 7.78 (t, 2H, J=7.5 Hz), 8.00 (t, 4H, J=7.5 Hz), 8.40 (d, 2H, J=7.5 Hz); MS (DCI—NH₃) m/e 541 (M+H)⁺.

EXAMPLE 35

Preparation of 4,4-bis(4-(2-quinolylmethoxy)phenyl)acetic acid-N-carboxymethyl amide

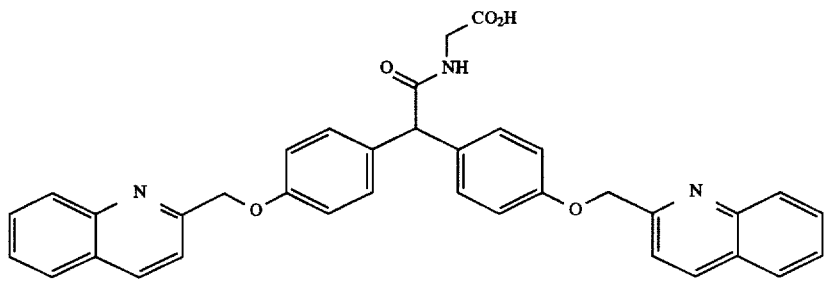

Step 1: 2,2-bis(4-hydroxyphenyl)acetic acid-N-carboxymethyl amide

To a stirred solution in CH₂Cl₂ (0.5 mL), THF (20 mL), and pyridine (20 mL) of 2,2-bis(4-hydroxyphenyl)acetic acid (0.94 g, 3.85 mmol), prepared as in Example 31, was added 1-(3-dimethylaminopropyl)-3-ethylcarbodiimide (1.10 g, 5.76 mmol), glycine methyl ester hydrochloride (0.723 g, 5.76 mmol), and N-methylmorpholine (0.63 mL, 5.76 mmol) and the mixture was stirred overnight at room temperature. The reaction mixture was then diluted with ethyl acetate and aqueous 0.5 N HCl. The organic layer was washed with 0.5 N HCl (3X), saturated aqueous NaHCO₃ (3X), and brine, dried over MgSO₄, filtered, and concentrated in vacuo. The residue was dried to constant weight on high vacuum to give 1.05 g (87%) of 2,2-bis(4-hydroxyphenyl)acetic acid-N-carboxymethyl amide.

Step 2: 44-bis(4-(2-quinolylmethoxy)phenyl)acetic acid-N-carboxymethyl amide

The desired compound was prepared according to the method of Example 1, steps 1–3, except substituting 2,2-bis(4-hydroxyphenyl)acetic acid-N-carboxymethyl amide, prepared as in step 1, for 4,4-bis(4-hydroxyphenyl)pentanoic acid: mp 228°–231° C.; ¹H NMR (300 MHz, DMSO—d₆) d 3.79 (d, 2H, J=6.5 Hz), 4.93 (s, 1H), 5.34 (s, 4H), 7.00 (d, 4H, J=7.5 Hz), 7.22 (d, 4H, J=7.5), 7.63 (m, 4H), 7.79 (t, 2H, J=7.5 Hz), 8.01 (m, 4H), 8.44 (m, 3H), 12.52 (s, 1H); MS (DCI—NH₃) m/e 584 (M+H)⁺. Anal. Calc'd. for $C_{36}H_{29}N_3O_5$: C, 74.08; H, 5.01; N, 7.20. Found: C, 73.81; H, 5.20; N, 6.90.

EXAMPLE 36

Preparation of [3,3-bis-(2-quinolylmethoxyphenyl)-but-1-yl]-2-iminoxypropionic acid Step 1: 3,3-bis(4-(2-quinolylmethoxy)phenyl)butan-1-ol To a 0° C. solution in THF (40 mL) of 3,3-bis(4-(2-quinolylmethoxy)phenyl)-butanoic acid ethyl ester (3.2 g, 5.5 mmol), prepared as in Example 13, was added slowly a solution of LiAlH₄ (1.0M, 6 mL, 6.0 mmol). The mixture was stirred for 2 hours and water (15 mL) was added slowly followed by aqueous 1N NaOH. The reaction mixture was diluted with THF (20 mL) and the mixture was filtered through a celite pad. The filtrate was extracted with ether and the organic extract was washed with water and brine, dried over MgSO$_4$, filtered, and concentrated in vacuo to provide 3,3-bis(4-(2-quinolylmethoxy)phenyl)butan-1-ol (2.4 g) as a pale yellow foam.

Step 2: O-[4,4-bis(4-(2-quinolylmethoxy)phenyl)but-1-yl] hydroxylamine

The desired compound was prepared according to the method of Example 5, steps 1 and 2, except substituting 3,3-bis(4-(2-quinolylmethoxy)phenyl)butan-1-ol, prepared as in step 1, for 4,4-bis(4-(2-quinolylmethoxy)phenyl) pentan-1-ol.

Step 3: [3,3-bis-(2-quinolylmethoxyphenyl)but-1-yl]-2-iminoxypropionic acid

The desired compound was prepared according to the method of Example 6, except substituting O-[4,4-bis(4-(2-quinolylmethoxy)phenyl)but-1-yl]hydroxylamine for O-[4,4-bis(4-(2-quinolylmethoxy)phenyl)pent-1-yl] hydroxylamine: mp 94°–96° C.; $^1$H NMR (300 MHz, DMSO—d$_6$), d 1.58 (s, 3H), 1.80 (s, 3H), 2.39 (m, 2H), 3.85 (m, 2H), 5.32 (s, 4H), 6.97 (d, 4H, J=9 Hz), 7.11 (d, 4H, J=9 Hz), 7.64 (m, 4H), 7.78 (m, 2H), 7.99 (t, 4H, J=9 Hz), 8.41 (d, 2H, J=9 Hz). MS (FAB) m/e 626 (M+H)$^+$. Anal. Calc'd. for: C$_{39}$H$_{35}$N$_3$O$_5$·H$_2$O: C, 72.71; H, 5.47; N, 6.53. Found: C, 72.35; H, 5.42; N, 6.40.

EXAMPLE 37

Preparation of 4,4-bis(4-(2-quinolylmethoxy) phenyl)-4-hydroxy-2-butynoic acid

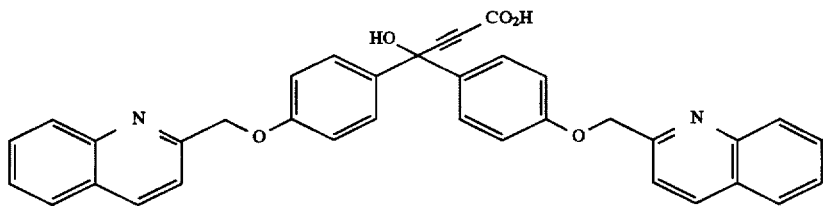

Step 1: 4,4-bis(2-quinolylmethoxy)phenyl)-4-hydroxy-2-butynoic acid methyl ester To a –78° C. solution in THF (40 mL) of bis(4-(2-quinolylmethoxy)phenyl) ketone (980 mg, 2 mmol), prepared as in Example 25, step 1, and propiolic acid (0.19 ml, 3 mmol) was added LDA (1.5M solution in THF, 4 mL, 6 mmol) and the mixture was left at room temperature for 24 hours. The reaction mixture was diluted with water, acidified to pH 5, and extracted with ethyl acetate. The organic phase was dried over MgSO$_4$, filtered, and concentrated in vacuo. The residue was dissolved in DMF (40 mL) and treated with methyl iodide (2 mL) and sodium bicarbonate (170 mg, 2 mmol). The reaction mixture was stirred for 24 hours and then was poured into water. The layers were separated and the aqueous phase was extracted with ethyl acetate. The combined organic phases were washed with brine, dried over MgSO$_4$, filtered, and concentrated in vacuo. Chromatography on silica gel (methylene chloride-ethyl acetate 4:1) provided 730 mg (63%) of 4,4-bis(2-quinolylmethoxy) phenyl)-4-hydroxy-2-butynoic acid methyl ester.

Step 2: 4,4-bis(4-(2-quinolylmethoxy)phenyl)-4-hydroxy-2-butynoic acid

The desired compound was prepared according to the method of Example 1, step 3, except substituting 4,4-bis(2-quinolylmethoxy)phenyl)-4-hydroxy-2-butynoic acid methyl ester, prepared as in step 1, for 4,4-bis(4-(2-quinolylmethoxy)phenyl)-pentanoic acid: mp 169°–172° C.; $^1$H NMR (300 MHz, DMSO—d$_6$) d 5.35 (s, 4H), 7.04 (d, 4H, J=9 Hz), 7.37 (d, 4H, J=9 Hz), 7.63 (m, 4H), 7.78 (m, 2H), 8.00 (m, 4H), 8.40 (d, 2H, J=8 Hz), 13.75 (bs, 1H); MS (DCI—NH$_3$) m/e: 567 (M+H)$^+$. Anal. Calc'd. for C$_{36}$H$_{26}$N$_2$O$_4$· 0.5 H$_2$O: C, 75.12; H, 4.73;N, 4.89. Found: 75.19; H, 4.80; N, 4.60.

EXAMPLE 38

Preparation of [5,5-bis(4-(2-quinolylmethoxy) phenyl)-5-hydroxy-3-pentyn-1-yl]-2-iminoxypropionic acid sodium salt

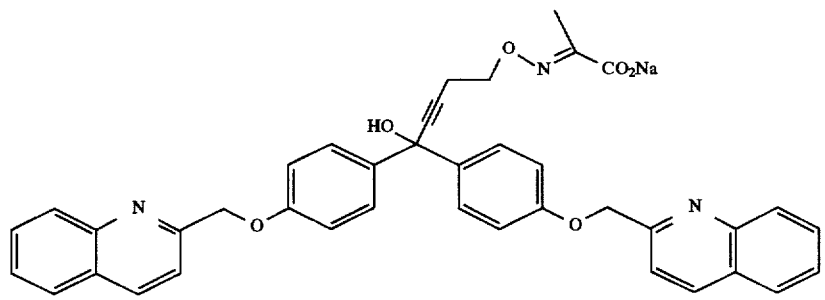

Step 1: 5,5-bis(4-(2-quinolylmethoxy)phenyl)-5-hydroxy-3-butyn-1-ol

To a −50° C. solution in THF (25 mL) of bis(4-(2-quinolylmethoxy)phenyl) ketone (496 mg, 1 mmol), prepared as in Example 25 was added a solution of dilithium salt of 3-butyn-1-ol (prepared by addition of 1.5M LDA (3 mL) to 3-bytyn-1-ol (0.15 mL, 2 mmol) at −50° C.) and the reaction mixture was allowed to warm to room temperature. The mixture was stirred for 12 hours at room temperature and then was quenched with saturated aqueous ammonium chloride. The layers were separated and the aqueous phase was extracted with ethyl acetate. The combined organic phases were washed with brine, dried over MgSO4, filtered, and concentrated in vacuo. Chromatography on silica gel (silica gel, ethyl acetate) provided 400 mg of 5,5-bis(4-(2-quinolylmethoxy)phenyl)-5-hydroxy-3-butyn-1-ol.

Step 2: [5,5-bis(4-(2-quinolylmethoxy)phenyl)-5-hydroxy-3-pentin-1-yl]-2-iminoxypropionic acid The desired compound was prepared according to the method of Example 36, steps 2, and 3, except substituting 5,5-bis(4-(2-quinolylmethoxy)phenyl)-5-hydroxy-3-butyn-1-ol ,prepared as in step 1, for 3,3-bis(4-(2-quinolylmethoxy)phenyl)butan-1-ol.

Step 3: [5,5-bis(4-(2-quinolylmethoxy)phenyl)-5-hydroxy-3-pentyn-1-yl]-2-iminoxypropionic acid sodium salt The desired compound was prepared according to the method of Example 2, except substituting [5,5-bis(4-(2-quinolylmethoxy)phenyl)-5-hydroxy-3-pentyn-1-yl]-2-iminoxypropionic acid, prepared as in Step 2, for 4,4-bis(4-(2-quinolylmethoxy)phenyl)pentanoic acid: mp 108°–111° C.; $^1$H NMR (300 MHz, DMSO—d$_6$) d: 1.83 (s, 3H), 2.61 (t, 2H, J=7 Hz), 4.10 (t, 2H, J=7 Hz), 5.32 (s, 4H), 6.96 (d, 4H, J=9 Hz), 7.40 (d, 4H, J=9 Hz), 7.62 (m, 4H), 7.78 (m, 2H) 8.00 (m, 4H), 8.40 (d, 2H, J=8 Hz); MS (FAB+) m/e 674 (M+Na)$^+$, 652 (M+H)$^+$, (FAB−) m/e 651 (M−H)$^−$. Anal. Calc'd. for C$_{40}$H$_{32}$N$_3$O$_6$Na.H$_2$: C, 69.46; H, 4.95; N, 6.07. Found: C, 69.62; H, 5.10; N, 5.61.

The following additional examples are prepared according to the method described in Example 1, except substituting the requisite heteroarylmethylhalide W-CH$_2$X where X is Cl, Br, or I for 2-chloromethylquinoline hydrochloride.

EXAMPLE 39

4,4-bis(4-(2-benzoxazolylmethoxy)phenyl)pentanoic acid

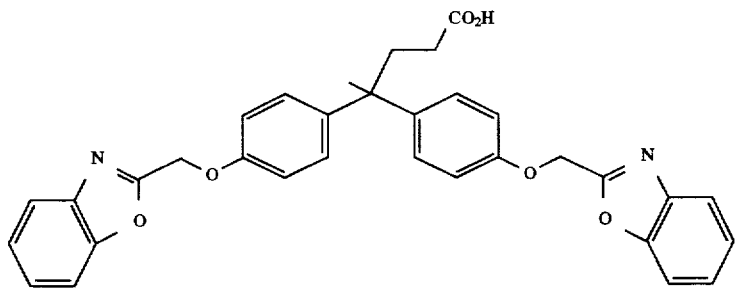

EXAMPLE 40

4,4-bis(4-(2-primidylmethoxy)phenyl)pentanoic acid

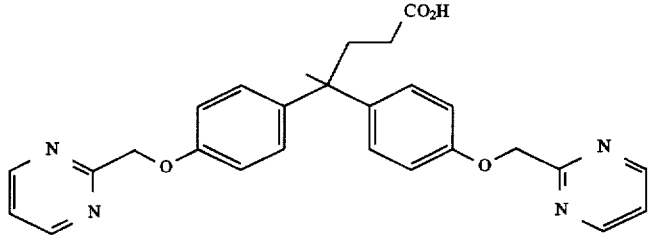

EXAMPLE 41
4,4-bis(4-(4-phenyl-2-thiazolylmethoxy)phenyl) pentanoic acid
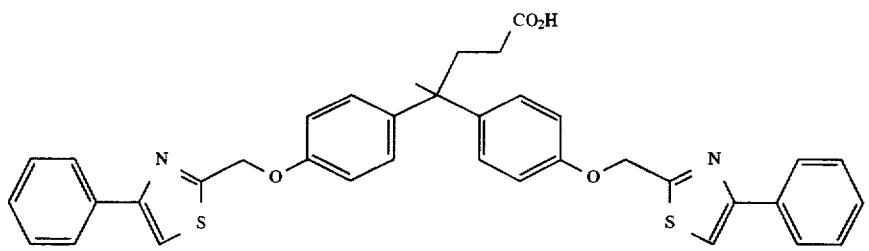
EXAMPLE 42
4,4-bis(4-(4-(pyrid-2-yl)-2-thiazolymethoxy) phenyl1)pentanoic acid
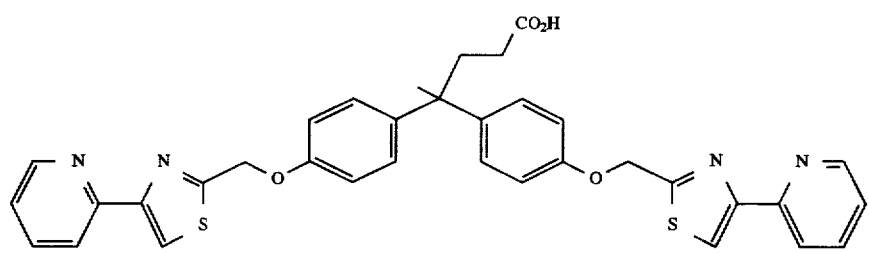
EXAMPLE 43
44-bis(4-(6-phenyl-2-pyridylmethoxy)phenyl) pentanoic acid
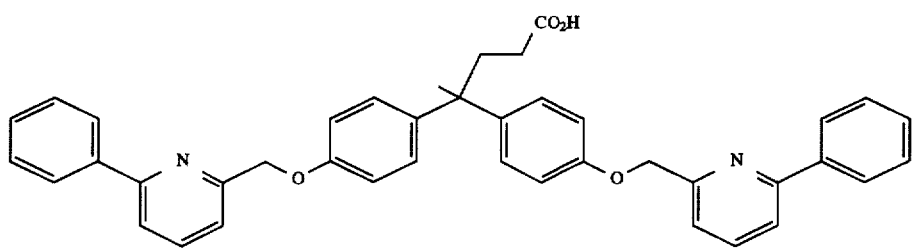
EXAMPLE 44
4,4-bis(4-(5-phenyl-2-pyridylmethoxy)phenyl) pentanoic acid
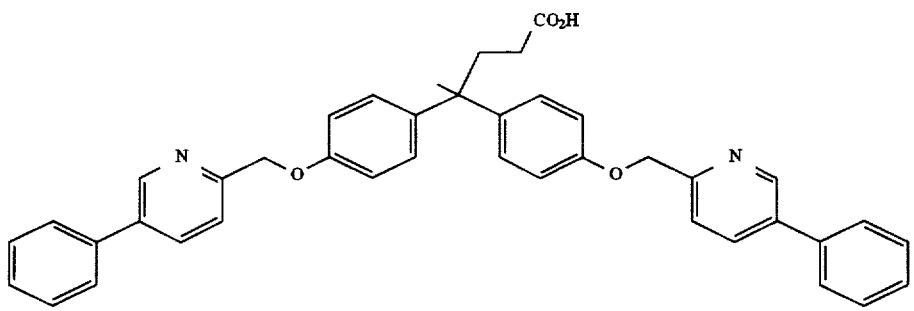

EXAMPLE 45

4,4-bis(4-(6-(pyrid-2-yl)-2-pyridylmethoxy)phenyl)pentanoic acid

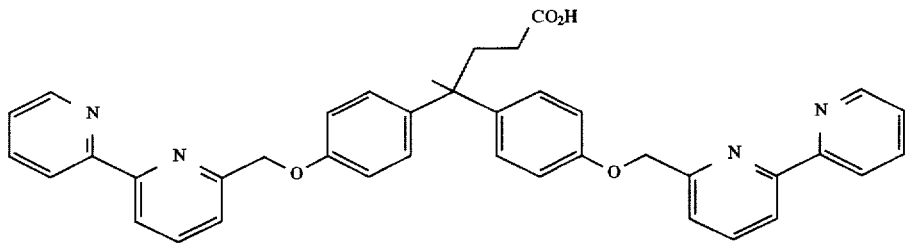

EXAMPLE 46

4,4-bis(4-(4-phenyl-2-pyrimidylmethoxy)phenyl)pentanoic acid

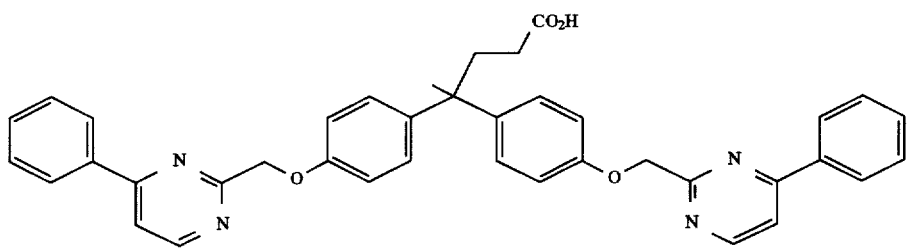

What is claimed is:

1. A compound of formula

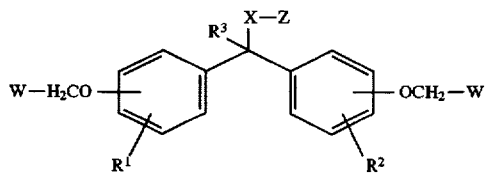

W is selected from the group consisting of
(a) quinolyl;
(b) quinolyl substituted with a substituent selected from the group consisting of
halogen,
alkyl of one to six carbon atoms,
phenyl,
phenyl substituted with a substituent selected from the group consisting of
halogen,
alkyl of one to six carbon atoms,
haloalkyl of one to six carbon atoms, and
alkoxy of one to six carbon atoms,
pyridyl,
pyridyl substituted with a substituent selected from the group consisting of
halogen,
alkyl of one to six carbon atoms, and
alkoxy of one to six carbon atoms;
(k) pyridyl;
(l) pyridyl substituted with a substituent selected from the group consisting of
phenyl,
phenyl substituted with a substituent selected from the group consisting of
halogen,
alkyl of one to six carbon atoms,
haloalkyl of one to six carbon atoms, and
alkoxy of one to six carbon atoms,
pyridyl,
pyridyl substituted with a substituent selected from the group consisting of
halogen,
alkyl of one to six carbon atoms, and
alkoxy of one to six carbon atoms;

$R^1$ and $R^2$ are independently selected from the group consisting of:
(a) hydrogen,
(b) alkyl of one to six carbon atoms,
(c) haloalkyl of one to six carbon atoms,
(d) alkoxy of one to six carbon atoms, and
(e) halogen;

$R^3$ is selected from the group consisting of
(a) hydrogen and
(b) alkyl of one to six carbon atoms;

X is absent or is selected from the group consisting of:
(a) alkylene of one to six atoms,
(b) alkenylene of one to six carbon atoms, and
(c) alkynylene of one to six carbon atoms;

Z is selected from the group consisting of:
(a) —COM,
(b) —CH=N—O—A—COM,
(c) —CH$_2$—O—N=A—COM, and
(d) —OR$^3$ where R$^3$ is hydrogen or alkyl of one to six carbon atoms wherein A is selected from the group consisting of
(a) alkylene of one to six carbon atoms, and
(b) cycloalkylene of three to eight carbon atoms; and M is selected from the group consisting of
(a) a pharmaceutically acceptable metabolically cleavable group, (b) —OR³ where R³ is selected from the group consisting of:
hydrogen, and
alkyl of one to six carbon atoms, and
(c) —NR⁷R⁸ where R⁷ and R⁸ are independently selected from the group consisting of:
hydrogen,
alkyl of one to six carbon atoms,
hydroxy, and
alkoxy of one to six carbon atoms,
or R⁷ and R⁸ taken together define a five- to eight-membered ring, with the proviso that R⁷ and R⁸ may not simultaneously be hydroxyl,
(d) —NR³SO₂R⁹ wherein R³ is as defined above and R⁹ is alkyl of one to six carbon atoms,
(e) —NH-tetrazolyl, and
(f) glycinyl.

2. A compound or pharmaceutically acceptable salt thereof as defined by claim 1 wherein Z is selected from the group consisting of
(a) COM,
(b) CH=N—O—A—COM,
(c) CH₂—O—N=A—COM, and
(d) OH wherein A is alkylene of one to six carbon atoms, and M is —OH.

3. A compound or pharmaceutically acceptable salt thereof as defined by claim 2 wherein W is the same at each occurrence and is selected from the group consisting of
(a) pyridyl,
(b) pyridyl substituted with a substituent selected from the group consisting of:
phenyl,
phenyl substituted with a substituent selected from the group consisting of:
halogen,
alkyl of one to six carbon atoms,
haloalkyl of one to six carbon atoms, or
alkoxy of one to six carbon atoms,
pyridyl, or
pyridyl substituted with a substituent selected from the group consisting of:
halogen,
alkyl of one to six carbon atoms, or
alkoxy of one to six carbon atoms.

4. A compound or pharmaceutically acceptable salt thereof as defined by claim 2 wherein W is the same at each occurrence and is selected from the group consisting of:
(a) quinolyl;
(b) quinolyl substituted with a substituent selected from the group consisting of
halogen,
alkyl of one to six carbon atoms,
phenyl,
phenyl substituted with a substituent selected from the group consisting of
halogen,
alkyl of one to six carbon atoms,
haloalkyl of one to six carbon atoms, and
alkoxy of one to six carbon atoms,
pyridyl,
pyridyl substituted with a substituent selected from the group consisting of
halogen,
alkyl of one to six carbon atoms, and
alkoxy of one to six carbon atoms.

5. A compound or pharmaceutically acceptable salt thereof as defined by claim 4 wherein W is the same at each occurrence and is selected from the group consisting of:
(a) quinolyl,
(b) quinolyl substituted with a substituent selected from the group consisting of:
halogen,
alkyl of one to six carbon atoms,
phenyl,
phenyl substituted with a substituent selected from the group consisting of
halogen,
alkyl of one to six carbon atoms,
haloalkyl of one to six carbon atoms, or
alkoxy of one to six carbon atoms;
pyridyl, or
pyridyl substituted with a substituent selected from the group consisting of:
halogen,
alkyl of one to six carbon atoms, and,
alkoxy of one to six carbon atoms.

6. A compound or pharmaceutically acceptable salt thereof as defined by claim 5 wherein W is the same at each occurrence and is selected from the group consisting of:
(a) quinolyl; and
(b) quinolyl substituted with a substituent selected from the group consisting of:
halogen,
alkyl of one to six carbon atoms,
phenyl,
phenyl substituted with a substituent selected from the group consisting of:
halogen,
alkyl of one to six carbon atoms,
haloalkyl of one to six carbon atoms, and
alkoxy of one to six carbon atoms;
pyridyl; and
pyridyl substituted with a substituent selected from the group consisting of:
halogen,
alkyl of one to six carbon atoms, and,
alkoxy of one to six carbon atoms.

7. A compound or pharmaceutically acceptable salt thereof as defined by claim 1 wherein Z is COM wherein M is —OH.

8. A compound or pharmaceutically acceptable salt thereof as defined by claim 7 wherein X is alkylene of one to six carbon atoms.

9. A compound or pharmaceutically acceptable salt thereof as defined by claim 8 wherein W is the same at each occurrence and is selected from the group consisting of:
(a) pyridyl;
(b) pyridyl substituted with a substituent selected from the group consisting of
phenyl,
phenyl substituted with a substituent selected from the group consisting of
halogen,
alkyl of one to six carbon atoms,
haloalkyl of one to six carbon atoms, and
alkoxy of one to six carbon atoms,
pyridyl,
pyridyl substituted with a substituent selected from the group consisting of
halogen,
alkyl of one to six carbon atoms, and
alkoxy of one to six carbon atoms.

10. A compound or pharmaceutically acceptable salt thereof as defined by claim 8 wherein W is the same at each occurrence and is selected from the group consisting of:

(a) quinolyl;
(b) quinolyl substituted with a substituent selected from the group consisting of
   halogen,
   alkyl of one to six carbon atoms,
   phenyl,
   phenyl substituted with a substituent selected from the group consisting of
      halogen,
      alkyl of one to six carbon atoms,
      haloalkyl of one to six carbon atoms, and
      alkoxy of one to six carbon atoms,
   pyridyl,
   pyridyl substituted with a substituent selected from the group consisting of
      halogen,
      alkyl of one to six carbon atoms, and
      alkoxy of one to six carbon atoms.

11. A compound or pharmaceutically acceptable salt thereof as defined by claim 8 wherein W is the same at each occurrence and is selected from the group consisting of:
(a) quinolyl;
(b) quinolyl substituted with a substituent selected from the group consisting of
   halogen,
   alkyl of one to six carbon atoms,
   phenyl,
   phenyl substituted with a substituent selected from the group consisting of
      halogen,
      alkyl of one to six carbon atoms,
      haloalkyl of one to six carbon atoms, and
      alkoxy of one to six carbon atoms,
   pyridyl,
   pyridyl substituted with a substituent selected from the group consisting of
      halogen,
      alkyl of one to six carbon atoms, and
      alkoxy of one to six carbon atoms.

12. A compound or pharmaceutically acceptable salt thereof as defined by claim 11 wherein W is the same at each occurrence and is selected from the group consisting of:
(a) quinolyl; and
(b) quinolyl substituted with a substituent selected from the group consisting of:
   halogen,
   alkyl of one to six carbon atoms,
   phenyl,
   phenyl substituted with a substituent selected from the group consisting of:
      halogen,
      alkyl of one to six carbon atoms,
      haloalkyl of one to six carbon atoms, and
      alkoxy of one to six carbon atoms;
   pyridyl; and
   pyridyl substituted with a substituent selected from the group consisting of:
      halogen,
      alkyl of one to six carbon atoms, and,
      alkoxy of one to six carbon atoms.

13. A compound or pharmaceutically acceptable salt thereof selected from the group consisting of:
4,4-bis(4-(2-quinolylmethoxy)phenyl)pentanoic acid,
4,4-bis(4-(2-quinolylmethoxy)phenyl)pentanoic acid sodium salt,
4,4-bis(4-(2-quinolylmethoxy)phenyl) pentanoic acid magnesium salt,
4,4-bis(4-(2-quinolylmethoxy)phenyl)pentan-1-ol,
(4,4-bis(4-(2-quinolylmethoxy)phenyl)pent-1-yl) iminoxyacetic acid,
(4,4-bis(4-(2-quinolylmethoxy)phenyl)pent-1 -yl)-2-iminoxypropionic acid,
(4,4-bis(4-(2-quinolylmethoxy)phenyl)pent-1-yl) oximinoacetic acid,
4,4-bis(4-(7-chloro-2-quinolylmethoxy)phenyl)pentanoic acid,
4,4-bis(4-(7-fluoro-2-quinolylmethoxy)phenyl)pentanoic acid sodium salt,
2,2-bis(4-(2-quinolylmethoxy)phenyl)propionic acid,
3,3-bis(4-(2-quinolylmethoxy)phenyl)butanoic acid,
5,5-bis(4-(2-quinolylmethoxy)phenyl)hexanoic acid,
5,5-bis(4-(2-quinolylmethoxy)phenyl)hexanoic acid sodium salt,
4,4-bis-(4-(2-pyridylmethoxy)phenyl)pentanoic acid sodium salt,
4,4-bis(3-chloro-4-(2-quinolylmethoxy)phenyl)pentanoic acid,
4,4-bis(3-chloro-4-(2-quinolylmethoxy)phenyl)pentanoic acid sodium salt,
(4,4-bis(3-chloro-4-(2-quinolylmethoxy)phenyl)pent-1-yl)-2-iminoxypropionic acid sodium salt,
4,4-bis(4-(2-quinolylmethoxy)phenyl)pentanoic acid N,N-diethylhydroxyl amino-O-ester,
2,2-bis(4-(2-quinolylmethoxy)phenyl)butyric acid,
1,1-bis(4-(2-quinolylmethoxy)phenyl)ethanol,
2,2-dimethyl-3,3-bis(4-(2-quinolylmethoxy)phenyl) propionic acid sodium salt,
(2,2-dimethyl-3,3-bis(4-(2-quinolylmethoxy)phenyl) prop-1-yl)oximinoacetic acid sodium salt,
2,2-dimethyl-3,3-bis(4-(2-quinolylmethoxy)phenyl)-1-propyliminoxyacetic acid,
2,2-bis(4-(2-quinolylmethoxy)phenyl)acetic acid,
2,2-bis(4-(6-fluoro-2-quinolylmethoxy)phenyl)acetic acid,
2,2-bis(4-(2-quinolylmethoxy)phenyl)eth-1-yloximinoacetic acid,
2,2-bis(4-(2-quinolylmethoxy)phenyl)eth-1-yloximinoacetic acid sodium salt,
3,3-bis(4-(2-quinolylmethoxy)phenyl)propionic acid,
3,3-bis(4-(2-quinolylmethoxy)phenyl)propionic acid sodium salt,
4,4-bis(4-(2-quinolylmethoxy)phenyl)acetic acid-N-carboxymethyl amide,
(3,3-bis-(2-quinolylmethoxyphenyl)but-1-yl)-2-iminoxypropionic acid,
4,4-bis(4-(2-quinolylmethoxy)phenyl)-4-hydroxy-2-butynoic acid, and
(5,5-bis(4-(2-quinolylmethoxy)phenyl)-5-hydroxy-3-pentyn-1-yl)-2-iminoxypropionic acid sodium salt.

14. A compound or pharmaceutically acceptable salt thereof selected from the group consisting of:
4,4-bis(4-(2-quinolylmethoxy)phenyl)pentanoic acid,
4,4-bis-(4-(2-quinolylmethoxy)phenyl)pentanoic acid sodium salt,
4,4-bis(4-(2-quinolylmethoxy)phenyl) pentanoic acid magnesium salt,
4,4-bis(4-(7-chloro-2-quinolylmethoxy)phenyl)pentanoic acid, 4,4-bis(4-(7-fluoro-2-quinolylmethoxy)phenyl)pentanoic acid sodium salt, 2,2-bis(4-(2-quinolylmethoxy)phenyl)propionic acid, 3,3-bis(4-(2-quinolylmethoxy)phenyl)butanoic acid, 5,5-bis(4-(2-quinolylmethoxy)phenyl)hexanoic acid, 5,5-bis(4-(2-quinolylmethoxy)phenyl)hexanoic acid sodium salt, 4,4-bis(3-chloro-4-(2-quinolylmethoxy)phenyl)pentanoic acid, 4,4-bis(3-chloro-4-(2-quinolylmethoxy)phenyl)pentanoic acid sodium salt, 2,2-bis(4-(2-quinolylmethoxy)phenyl)butyric acid, 2,2-dimethyl-3,3-bis(4-(2-quinolylmethoxy)phenyl)-1-propyliminoxyacetic acid, 2,2-bis(4-(2-quinolylmethoxy)phenyl)acetic acid, 2,2-bis(4-(6-fluoro-2-quinolylmethoxy)phenyl)acetic acid, 2,2-bis(4-(2-quinolylmethoxy)phenyl)propionic acid, and 2,2-bis(4-(2-quinolylmethoxy)phenyl)propionic acid sodium salt.

15. A method for inhibiting lipoxygenase activity or leukotriene biosynthesis in a mammal in need of such treatment comprising administering to the mammal a therapeutically effective amount of a compound of claim 1.

16. A composition for inhibiting lipoxygenase activity or the biosynthesis of leukotrienes comprising a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 5,795,900
DATED : August 18, 1998
INVENTOR(S) : Brooks, et. al.

It is certified that error appears in the above-identified patent and that said Letters Patent is hereby corrected as shown below:

Title page, item [75], inventors: change "Clint D." to --Clint D. W.--.

Signed and Sealed this

Second Day of May, 2000

Attest:

Q. TODD DICKINSON

*Attesting Officer*      *Director of Patents and Trademarks*